(12) United States Patent
Pavcnik et al.

(10) Patent No.: US 9,414,843 B2
(45) Date of Patent: Aug. 16, 2016

(54) VASCULAR OCCLUSION METHODS, SYSTEMS AND DEVICES

(75) Inventors: Dusan Pavcnik, Portland, OR (US); John A. Kaufman, Lake Oswego, OR (US); Thomas Osborne, Bloomington, IN (US); Brian Bates, Bloomington, IN (US); Umesh Patel, West Lafayette, IN (US); Clay D. Fette, Palm Beach Gardens, FL (US); Likang Chin, Cleveland Heights, OH (US); Chad S. McAlexander, Delphi, IN (US); Bhavin Shah, West Lafayette, IN (US)

(73) Assignees: Cook Medical Technologies LLC, Bloomington, IN (US); Cook Biotech Incorporated, West Lafayette, IN (US); Oregon Health & Science University, Portland, OR (US)

(*) Notice: Subject to any disclaimer, the term of this patent is extended or adjusted under 35 U.S.C. 154(b) by 1476 days.

(21) Appl. No.: 11/442,687

(22) Filed: May 26, 2006
(Under 37 CFR 1.47)

(65) Prior Publication Data

US 2007/0166345 A1 Jul. 19, 2007

Related U.S. Application Data

(63) Continuation of application No. PCT/US2004/039840, filed on Nov. 29, 2004.

(60) Provisional application No. 60/525,793, filed on Nov. 28, 2003, provisional application No. 60/557,248, filed on Mar. 29, 2004.

(51) Int. Cl.
*A61M 29/00* (2006.01)
*A61B 17/12* (2006.01)
(Continued)

(52) U.S. Cl.
CPC ...... *A61B 17/12109* (2013.01); *A61B 17/12022* (2013.01); *A61B 17/12181* (2013.01);
(Continued)

(58) Field of Classification Search
CPC ................... A61B 17/12022; A61B 17/12109; A61B 17/12159; A61B 17/1219; A61B 17/12181; A61B 2017/12054
USPC ........................... 606/194, 184, 108; 424/423
See application file for complete search history.

(56) References Cited

U.S. PATENT DOCUMENTS

| 4,218,782 A | 8/1980 | Ryagg |
| 4,585,458 A | 4/1986 | Kuland |

(Continued)

FOREIGN PATENT DOCUMENTS

| EP | 1543798 A2 | 6/2005 |
| EP | 1648347 | 4/2006 |

(Continued)

OTHER PUBLICATIONS

Gorisch et al., "Heat-Induced Contraction of Blood Vessels". Lasers in Surgery and Medicine, 1982; 2:1-13.
(Continued)

*Primary Examiner* — Corrine McDermott
*Assistant Examiner* — Sarah Simpson
(74) *Attorney, Agent, or Firm* — Woodard, Emhardt, Moriarty, McNett & Henry LLP

(57) ABSTRACT

Described are devices, methods and systems useful for achieving occlusion of vascular vessels. Percutaneous procedures are used to occlude and obliterate the greater saphenous vein, for example in the treatment of varicose vein condition caused by venous reflux. Certain embodiments encompass the deployment of one or more vascular occlusion devices via a through-and-through percutaneous procedure that leaves the vascular occlusion device or devices in a through-and-through condition.

31 Claims, 40 Drawing Sheets

(51) Int. Cl.
  *A61B 17/00* (2006.01)
  *A61B 17/3205* (2006.01)

(52) U.S. Cl.
  CPC ..... *A61B17/00008* (2013.01); *A61B 17/32053* (2013.01); *A61B 2017/12054* (2013.01); *A61L 2430/36* (2013.01)

(56) References Cited

U.S. PATENT DOCUMENTS

| | | | |
|---|---|---|---|
| 5,061,245 | A | 10/1991 | Waldvogel et al. |
| 5,156,620 | A | 10/1992 | Pigott |
| 5,411,552 | A | 5/1995 | Andersen et al. |
| 5,607,465 | A | 3/1997 | Camilli |
| 5,609,598 | A | 3/1997 | Laufer et al. |
| 5,720,776 | A | 2/1998 | Chuter et al. |
| 5,810,847 | A | 9/1998 | Laufer et al. |
| 5,885,601 | A | 3/1999 | Sokal |
| 6,014,589 | A | 1/2000 | Farley et al. |
| 6,033,398 | A | 3/2000 | Farley et al. |
| 6,036,687 | A | 3/2000 | Laufer et al. |
| 6,071,277 | A | 6/2000 | Farley et al. |
| 6,110,201 | A | 8/2000 | Quijano et al. |
| 6,126,686 | A | 10/2000 | Badylak et al. |
| 6,152,899 | A | 11/2000 | Farley et al. |
| 6,165,172 | A | 12/2000 | Farley et al. |
| 6,168,614 | B1 | 1/2001 | Andersen et al. |
| 6,179,832 | B1 | 1/2001 | Jones et al. |
| 6,200,312 | B1 | 3/2001 | Zikorus et al. |
| 6,200,336 | B1 | 3/2001 | Pavcnik et al. |
| 6,206,931 | B1 | 3/2001 | Cook et al. |
| 6,287,334 | B1 | 9/2001 | Moll et al. |
| 6,299,637 | B1 | 10/2001 | Shaolian et al. |
| 6,432,116 | B1 * | 8/2002 | Callister et al. ............... 606/157 |
| 6,508,833 | B2 | 1/2003 | Pavcnik et al. |
| 6,530,956 | B1 | 3/2003 | Mansmann |
| 6,582,462 | B1 | 6/2003 | Andersen et al. |
| 6,666,892 | B2 | 12/2003 | Hiles et al. |
| 6,716,241 | B2 | 4/2004 | Wilder et al. |
| 6,723,116 | B2 * | 4/2004 | Taheri .......................... 623/1.11 |
| 6,752,828 | B2 | 6/2004 | Thornton |
| 7,316,695 | B2 * | 1/2008 | Mialhe .......................... 606/158 |
| 2001/0011187 | A1 | 8/2001 | Pavcnik et al. |
| 2001/0039450 | A1 * | 11/2001 | Pavcnik et al. .............. 623/1.24 |
| 2002/0103542 | A1 | 8/2002 | Bilbo |
| 2002/0123800 | A1 | 9/2002 | Taheri |
| 2002/0188348 | A1 | 12/2002 | DiMatteo et al. |
| 2003/0036795 | A1 | 2/2003 | Andersen et al. |
| 2003/0051735 | A1 * | 3/2003 | Pavcnik et al. ............... 128/831 |
| 2003/0130726 | A1 | 7/2003 | Thorpe et al. |
| 2003/0191525 | A1 | 10/2003 | Thornton |
| 2003/0208261 | A1 | 11/2003 | Thorpe et al. |
| 2004/0015230 | A1 | 1/2004 | Moll et al. |
| 2004/0039246 | A1 | 2/2004 | Gellman et al. |
| 2004/0049262 | A1 | 3/2004 | Obermiller et al. |
| 2004/0082989 | A1 * | 4/2004 | Cook et al. ................... 623/1.13 |
| 2004/0193253 | A1 | 9/2004 | Thorpe et al. |
| 2004/0254589 | A1 * | 12/2004 | Darnis et al. ................. 606/139 |
| 2005/0090860 | A1 * | 4/2005 | Paprocki ....................... 606/213 |
| 2005/0096735 | A1 * | 5/2005 | Hojeibane et al. ........... 623/1.24 |

FOREIGN PATENT DOCUMENTS

| | | |
|---|---|---|
| GB | 2423934 A | 9/2006 |
| GB | 2432845 A | 6/2007 |
| WO | WO 94/17841 A1 | 8/1994 |
| WO | WO 97/37614 A1 | 10/1997 |
| WO | WO 99/19005 A1 | 4/1999 |
| WO | WO 00/32112 A1 | 6/2000 |
| WO | WO 00/45691 | 8/2000 |
| WO | WO 01/19285 | 3/2001 |
| WO | WO 01/70091 | 9/2001 |
| WO | WO 01/70091 A2 | 9/2001 |
| WO | WO 03/002168 | 1/2003 |
| WO | WO 03/009764 A1 | 2/2003 |
| WO | WO 03/043506 A1 | 3/2003 |
| WO | WO 03/070124 | 8/2003 |

OTHER PUBLICATIONS

Luo et al., "Direct intrahepatic portacaval shunt: an experimental study". World Journal of Gastroenterology, 2003; 9(2):324-328.

Min et al., "Endovenous Laser Treatment of Saphenous Vein Reflux: Long-Term Results". Journal of Vascular and Interventional Radiology, Aug. 2003, vol. 14; No. 8:991-996.

* cited by examiner

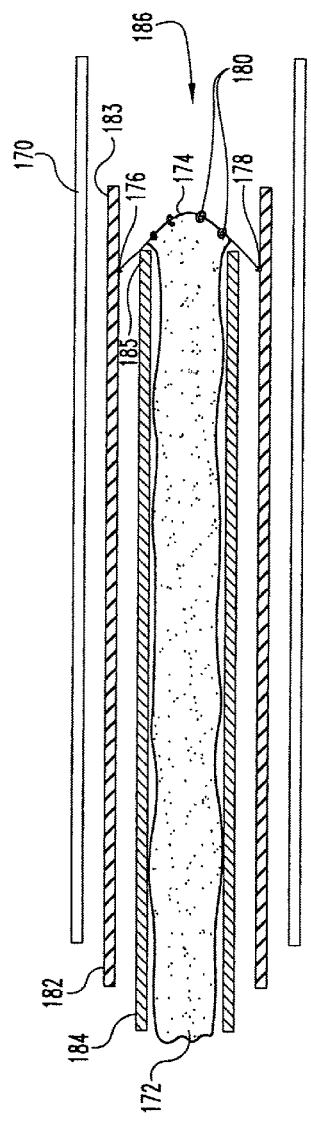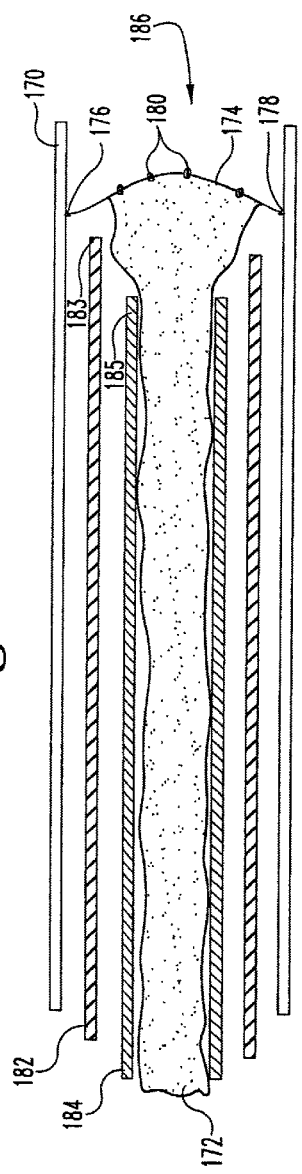

VASCULAR OCCLUSION METHODS, SYSTEMS AND DEVICES

STATEMENT OF RELATED APPLICATIONS

This application is a continuation application of PCT Application No. PCT/US2004/039840 filed Nov. 29, 2004, which claims the benefit of U.S. Provisional Patent Application Ser. No. 60/525,793 filed Nov. 28, 2003 and U.S. Provisional Patent Application Ser. No. 60/557,248 filed Mar. 29, 2004, all of which are incorporated herein by reference.

BACKGROUND

The present invention resides generally in the field of devices and methods useful for the occlusion of vascular vessels, and in a particular aspect relates to the occlusion of the greater or lessor saphenous vein to treat complications, such as varicose vein condition, resultant of venous reflux.

As further background, the human venous system generally includes a superficial venous system and a deep venous system, with perforating veins connecting the two systems. In human legs, the superficial system includes the great saphenous vein and the short saphenous vein. The deep system of the legs includes the anterior and posterior tibial veins which join to form the popliteal vein, which becomes the femoral vein when united with the short saphenous vein.

Such venous systems are designed to carry blood back to the heart. To facilitate this function, the venous systems contain one-way valves, which are typically bicuspid. The failure of venous valves leads to retrograde flow or reflux within the venous system. This can result in various venous diseases which include varicose veins and chronic venous insufficiency. In the varicose vein condition, the superficial veins of the leg become dilated and tortuous and can result in discoloration, pain and ulceration. The varicose vein condition commonly involves the incompetence of one or more venous valves which allow reflux of blood from the deep venous system to the superficial venous system or reflux within the superficial system. In many cases, blood from the deep vein system refluxes back down the greater saphenous vein leading to varicosity within superficial veins below the greater saphenous vein.

Surgical stripping of the greater saphenous vein is an extensively practiced technique for treating the varicose vein condition. In this technique, an incision is made in the groin to expose the sapheno-femoral junction, where the great saphenous vein and its branches are ligated. The distal portion of the greater saphenous vein has been exposed by incision interior to the medial inalleolus, and a stripping device is introduced to exit from the proximal saphenous vein. After holding the leg vertical for a time to empty the venous tree, the vein is stripped from the ankle to the groin. In cases wherein the small saphenous vein is also incompetent, it is stripped at the same time from an incision posterior to the lateral malleolus to the popliteal space. After stripping, the leg is held vertically for a time to permit vessel ends to retract, constrict and clot. The stripping procedure is commonly followed by the removal of collateral veins working through small incisions using an avulsion-extraction technique.

More recently, techniques have been developed to try to avoid the invasive stripping procedure and its associated complications. For example, techniques and devices have been developed to treat the varicose vein condition with radiofrequency (RF) energy. In these techniques a catheter having an electrode tip is used to deliver RF energy within the vein to be treated. The RF energy causes localized heating and shrinkage of the venous tissue. The electrodes can be drawn through or repositioned within the vein to treat different sections or segments of the vein. For additional information on RF treatments and devices, reference can be made for example to U.S. Pat. Nos. 6,200,312, 6,179,832, 6,165,172, 6,152,899, 6,071,277, 6,036,687, 6,033,398, 6,014,589, and 5,609,598.

Another technique which has been developed is the endovenous laser technique. This technique is typically performed under local or regional anesthesia. A bare laser fiber is inserted into the diseased vein and delivers laser light in a pulsed fashion to heat the vein to cause damage and constriction. See, e.g., Gorisch et al., "Heat Induced Contraction of Blood Vessels", Laser Surgery Medicine 2(1), 1-13(1982). Other techniques for treating the varicose vein condition includes sclerotherapy, in which a sclerosing solution is injected into the vein to damage the interior of the vein, followed by compression wrapping to facilitate permanent closure of the damaged vein. Phlebectomy is a procedure also utilized to treat varicose veins, typically medium sized and larger veins. In this procedure, small stab incisions are made in the skin and a tool is used to hook and pull the vein out through the incision.

In view of this background, the need remains for improved and alternative techniques, devices and systems for affecting the venous system to treat venous conditions. The present invention is addressed to these needs.

SUMMARY OF THE INVENTION

Accordingly, in one aspect, the present invention provides a method for treating venous reflux in a leg of a human. The method includes percutaneously accessing a saphenous vein of the leg, and inserting a percutaneous delivery device in the saphenous vein. An occlusion device is delivered into the saphenous vein from the delivery device, so as to occlude the saphenous vein and prevent reflux therethrough.

In another aspect, the invention provides a method for occluding a vascular vessel. The method includes providing a percutaneous delivery device extending between an entry opening and an exit opening in the vessel. An occluder is delivered into the vessel from the delivery device, wherein the occluder extends between the entry opening and the exit opening.

The invention also concerns a method for occluding a vascular vessel that includes providing first and second openings in the vessel. An occluder is positioned in the vessel and extends between the first and second openings.

In another aspect, the invention provides a method for treating a refluxing greater saphenous vein in a human. The method includes delivering into the greater saphenous vein a resorbable occlusion device so as to occlude and prevent reflux through the vein.

In another embodiment, the invention provides an occlusion device useful for occluding a greater saphenous vein of a human. The occluder device has an elongated occluder body having a length of at least about 10 centimeters. The occluder body is configured for passage through a percutaneous delivery device and into the greater saphenous vein so as to cause occlusion of the vein.

The invention also provides a medical system for vascular occlusion that includes an elongate occluder body having a length of at least about 10 centimeters, and a cannulated device configured for delivery of the elongate occluder body into a vascular vessel.

In another aspect, the invention provides a system for delivery of an elongate vascular occluder. The system includes an elongate puncture device for puncturing a vascular vessel, and a guiding catheter having a lumen for receiving the elongate puncture device. This system further includes a sheath for passage over the guiding catheter, and an elongate guide wire passable through the sheath and configured for attachment to an elongate vascular occluder to pull the occluder into the sheath.

The invention also provides a medical assembly useful for the delivery of an elongate vascular occluder. The assembly includes an elongate puncture device for puncturing a vascular vessel, and a guiding catheter having a lumen for receiving the elongate puncture device. A first sheath is provided for passage over the guiding catheter, and a second sheath is provided for passage through the first sheath and configured to contain the elongate vascular occluder.

Further provided by the invention, is a vascular occluder device that includes an elongate occluder body, wherein the body also has an adaptation for attachment to a pulling device.

In another embodiment, the invention provides a method for occluding a saphenous vein of a human. The method includes accessing the saphenous vein with an introducer needle. A puncture wire is passed into the saphenous and used to exit the saphenous vein at a location spaced from the access opening. A sheath is passed from the access opening to the exit opening, and an elongate occluder device is delivered into the saphenous vein from the sheath.

The present invention provides improved methods, systems and devices for occluding venous and other vascular vessels. Additional embodiments as well as features and advantages of the invention will be apparent from the further descriptions herein.

BRIEF DESCRIPTION OF THE DRAWINGS

FIGS. 20N-20P depict an illustrative occlusion device and an illustrative deployment embodiment of the invention.

DETAILED DESCRIPTION

Figure 1:
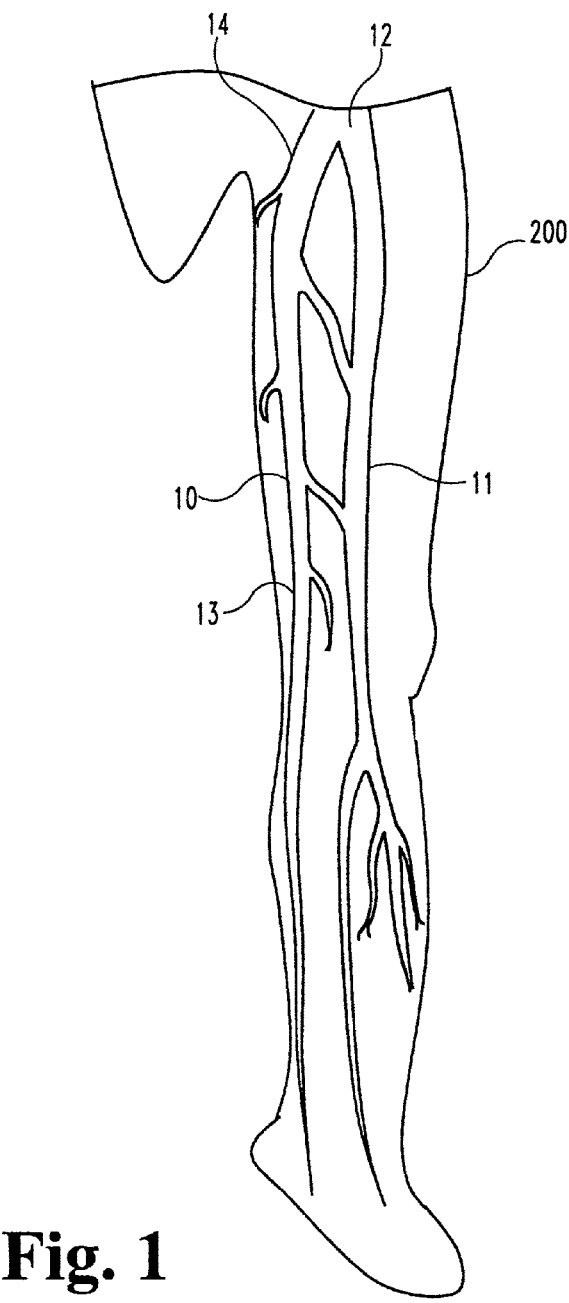
FIG. 1 depicts a human leg showing certain venous structures therein.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated devices, and further applications of the principles of the invention as illustrated therein are herein contemplated as would normally occur to one skilled in the art to which the invention relates.

As disclosed above, certain embodiments of the present invention provide methods, devices and systems for achieving occlusion of a vascular vessel such as a saphenous vein. Methods of the invention can be performed, for instance, in order to treat venous reflux through the greater saphenous vein such as that involved in the varicose vein condition.

Figure 2:
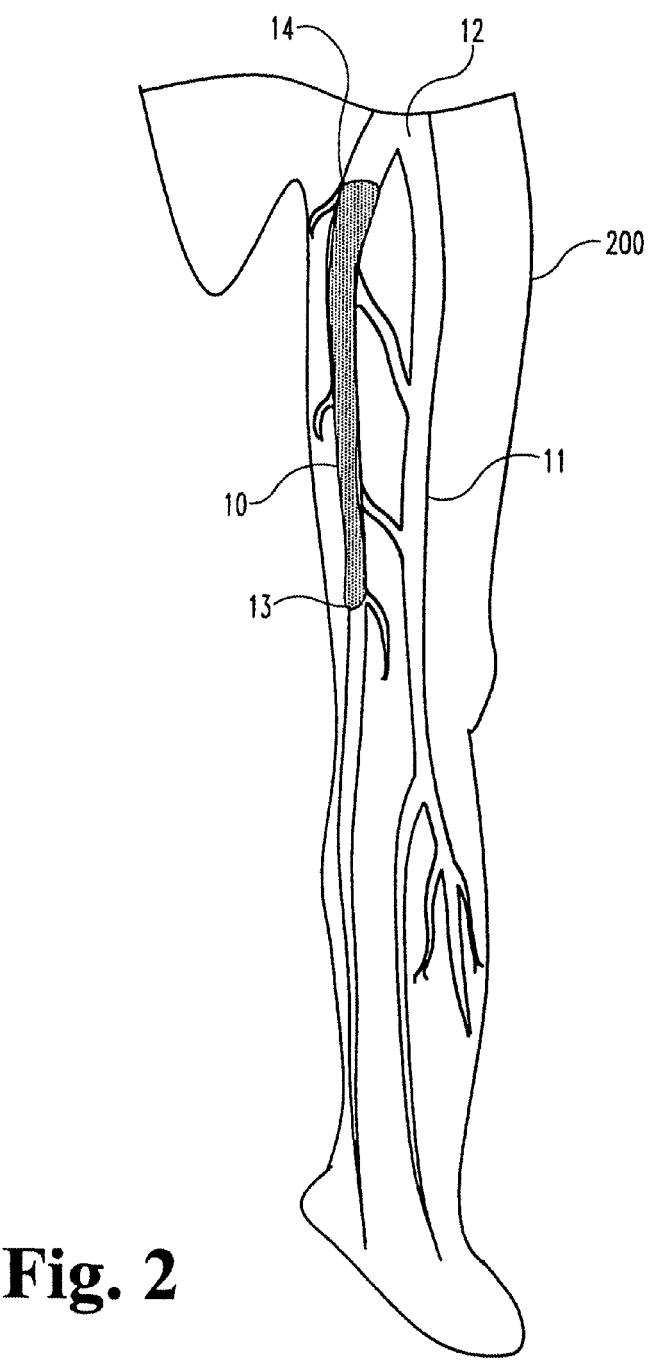
FIG. 2 depicts a human leg showing certain venous structures therein.

With reference now more particularly to the figures, shown in FIG. 1 is a diagram of a human leg showing certain venous structures therein. In particular, shown is human leg 200 having greater saphenous vein 10 and the femoral vein 11 which adjoin at the sapheno-femoral junction 12. In accordance with certain aspects of the present invention, greater saphenous vein 10 is occluded in a region constituting substantially all of the passage between a point 13 occurring near the medial side of the knee to a point 14 occurring prior to the sapheno-femoral junction 12, as illustrated by the shaded area in FIG. 2. Desirably, such occlusion is effective to prevent reflux of venous blood from the sapheno-femoral junction 12 in a direction down toward the medial side of the knee (e.g. at point 13). Such occlusion is effective to treat varicosities that commonly occur in lower portions of the leg, e.g. portions occurring below the knee.

Figure 3:
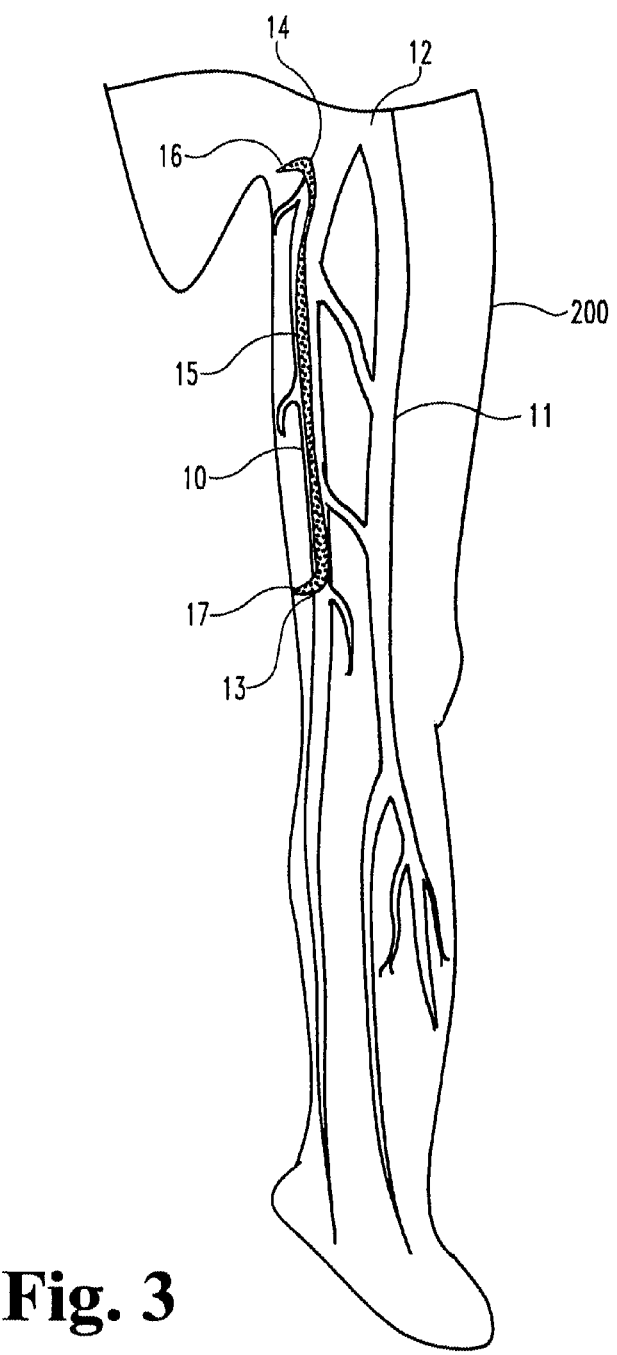
FIG. 3 depicts an illustrative embodiment of a human leg having an occlusion device of the invention located in the greater saphenous vein.

With reference now to FIG. 3, in certain forms of the invention, occlusion of the passage of the greater saphenous vein occurring between points 13 and 14 is achieved by an elongate occlusion device 15 that extends from point 13 to point 14, and that may include end portions 16 and 17 that traverse the wall of the greater saphenous vein 10. This may be achieved by deploying occlusion device 15 during a through-and-through percutaneous procedure, e.g. as described hereinbelow. It will be understood, however, that other occlusion devices may be used in aspects of the present invention, including those others disclosed herein as well as conventional devices such as coils.

Figure 4:
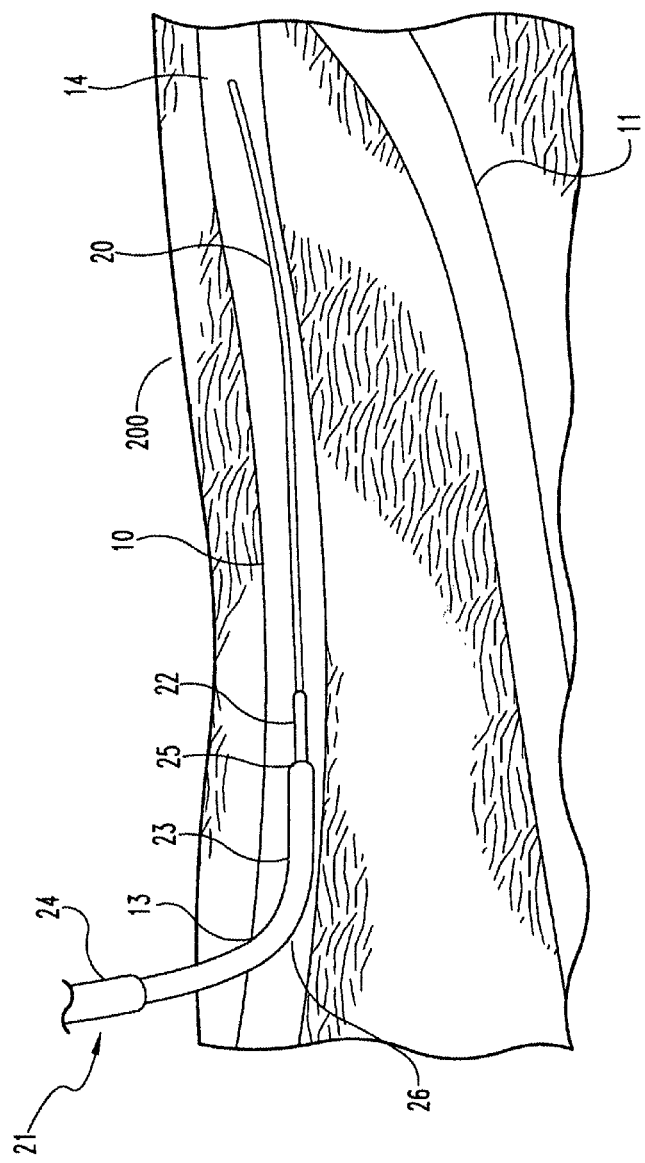
FIG. 4 depicts an illustrative deployment embodiment of the invention in that portion of the human leg occurring generally between points 13 and 14 in FIG. 1.

With reference now to FIG. 4, shown is an enlarged view of that portion of the human leg occurring generally between points 13 and 14 of FIG. 1. In an illustrative deployment procedure, percutaneous access to the greater saphenous vein 10 is achieved at point 13 using the Seldinger or any other suitable technique. For instance, an access needle can be passed through the skin to access greater saphenous vein 10, and a wire guide 20 can be passed through the access needle and into the vein 10. Prior to deployment of an occlusion device, wire guide 20 can be used for any number of conventional procedures including catheterization and imaging procedures in order to locate the sapheno-femoral junction 12 and discern a desired exit point 14 for a through-and-through percutaneous procedure. After any such preliminary procedures that are performed, wire guide 20 can be used in a deployment procedure for an occlusion device.

Specifically, referring still to FIG. 4, a deployment assembly 21 includes a flexible catheter 22, such as a 5 French radiopaque Teflon catheter, a guide sheath 23, such as a 7 French radiopaque guide sheath, a stiffening cannula received within guide sheath 23 (not shown in FIG. 4), and a delivery sheath 24 received over guide sheath 23. Guide sheath 23 includes a tapered distal end 25 and a bend 26 adjacent the distal end 25, generally corresponding to a bend in the stiffening cannula. Deployment assembly 21 is pre-assembled and threaded along guide wire 20 for the deployment procedure.

Figure 5:
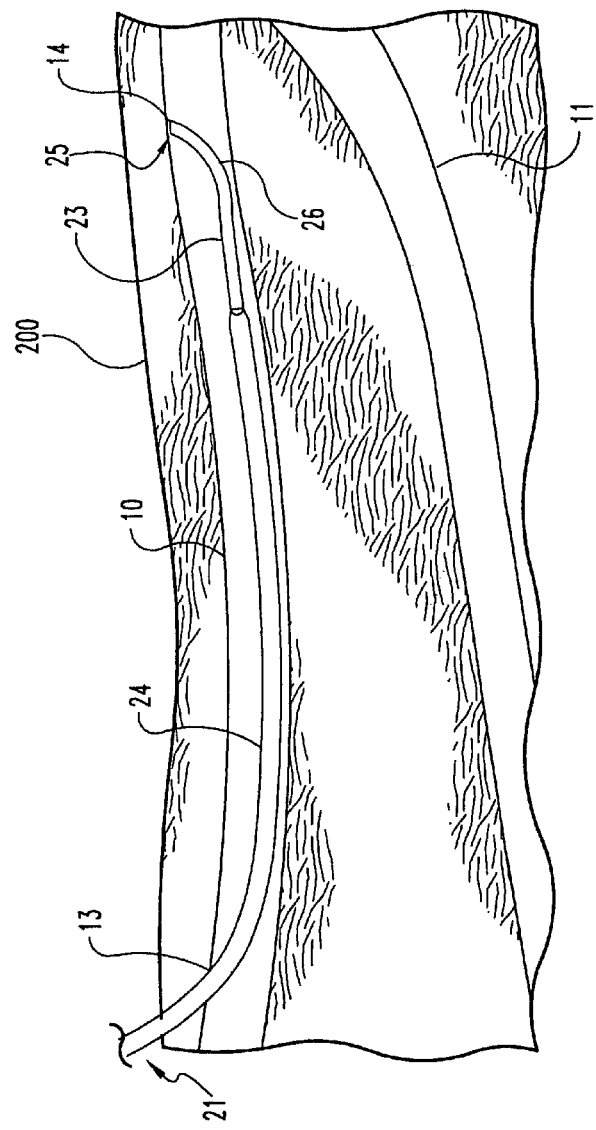
FIG. 5 depicts an illustrative deployment embodiment of the invention in that portion of the human leg occurring generally between points 13 and 14 in FIG. 1.

With reference now to FIG. 5, shown is deployment assembly 21 now received within greater saphenous vein 10 from point 13 to point 14, with the tapered distal end 25 of the guide sheath 23 positioned against the wall of greater saphenous vein 10 using the bend 26 to achieve rotation and placement of the end 25 of the guide sheath 23.

Figure 6:
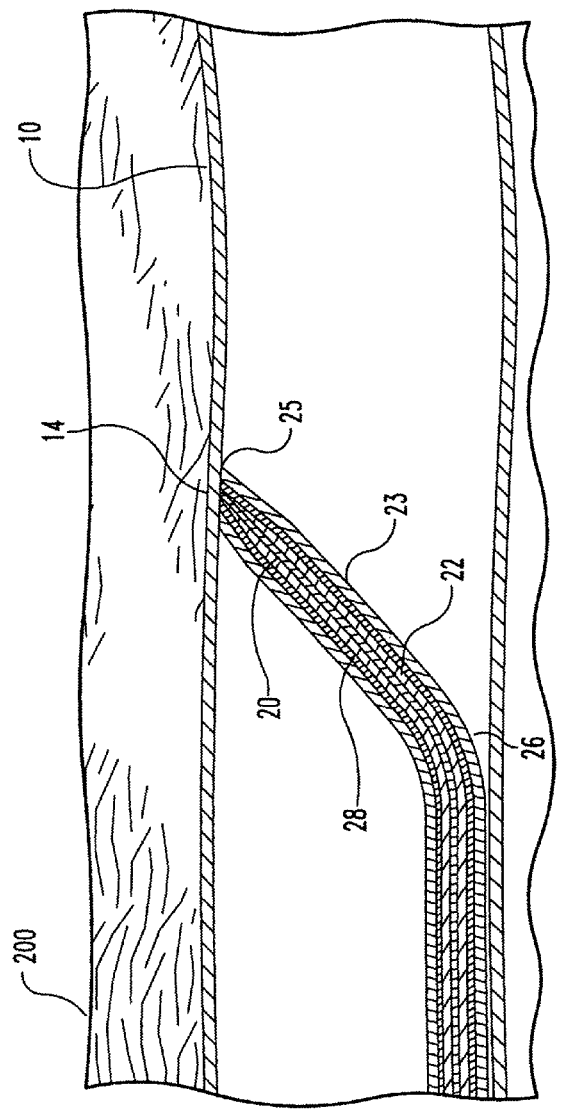
FIG. 6 depicts an illustrative deployment method of the present invention.
Figure 7:
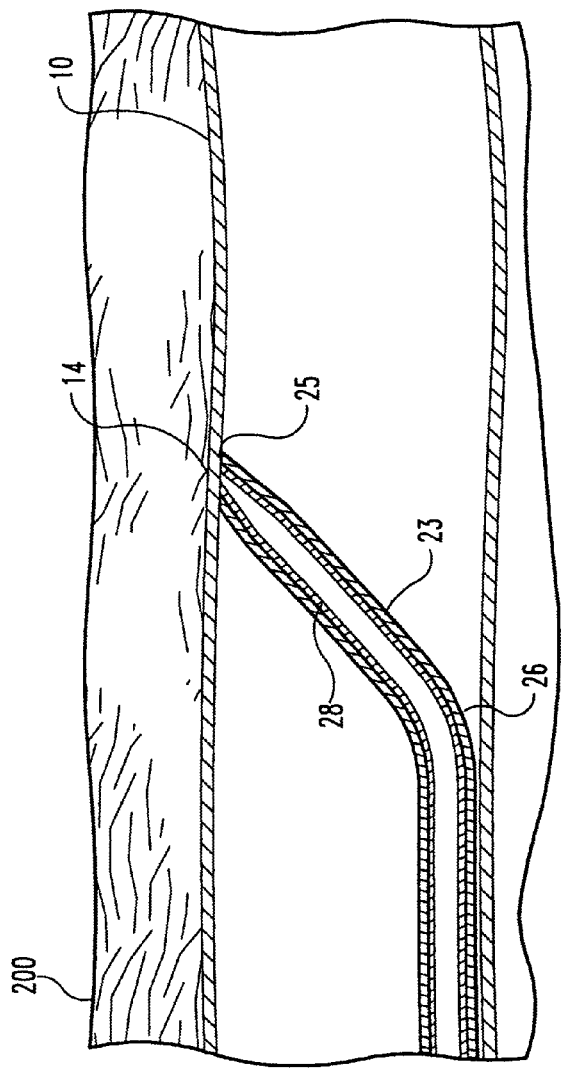
FIG. 7 depicts an illustrative deployment method of the present invention.

Reference will now be made to FIG. 6-12, which provide enlarged cross-sectional views in and around exit point 14 of greater saphenous vein 10 and illustrate various stages of a percutaneous exit procedure. Particularly, shown in FIG. 6 is a cross-sectional view of the stage of the procedure illustrated in FIG. 5. Tapered end 25 of guide sheath 23 is shown positioned against the wall of greater saphenous vein 10 at point 14. Received immediately within guide sheath 23 is stiffening cannula 28, which for example may be made from 14 gauge stainless steel. Received immediately within stiffening cannula 28 is guide catheter 22; and, received within guide catheter 22 is guide wire 20. In a next stage of the procedure, guide wire 20 and guide catheter 22 are withdrawn from the deployment assembly leaving a condition as illustrated in FIG. 7 with guide sheath 23 and stiffening cannula 28 remaining in place.

Figure 8:
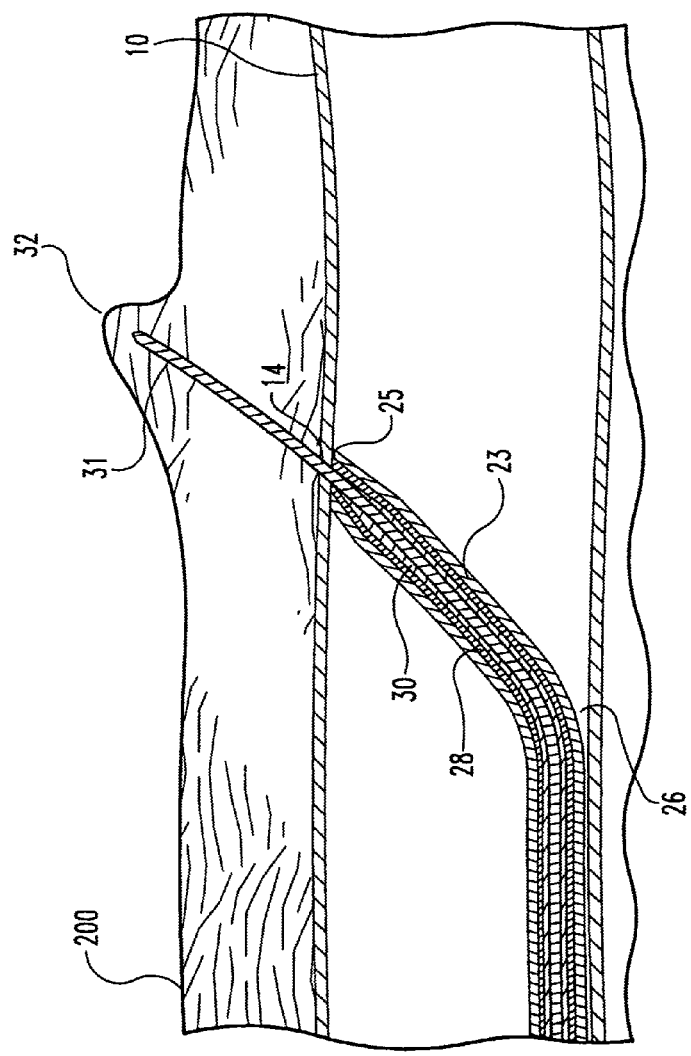
FIG. 8 depicts an illustrative deployment method of the present invention.
Figure 9:
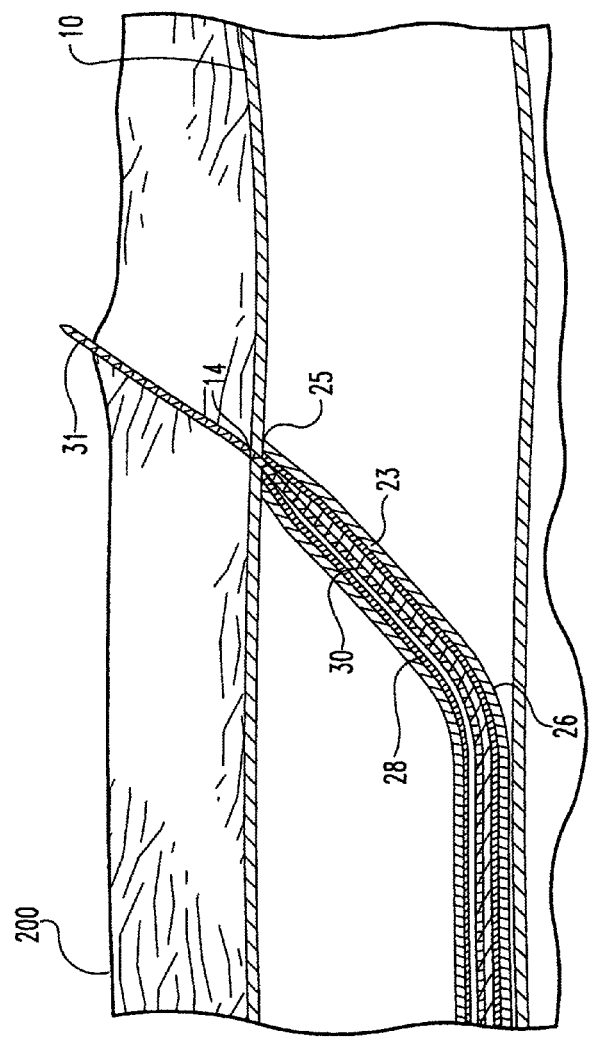
FIG. 9 depicts an illustrative deployment method of the present invention.
Figure 10:
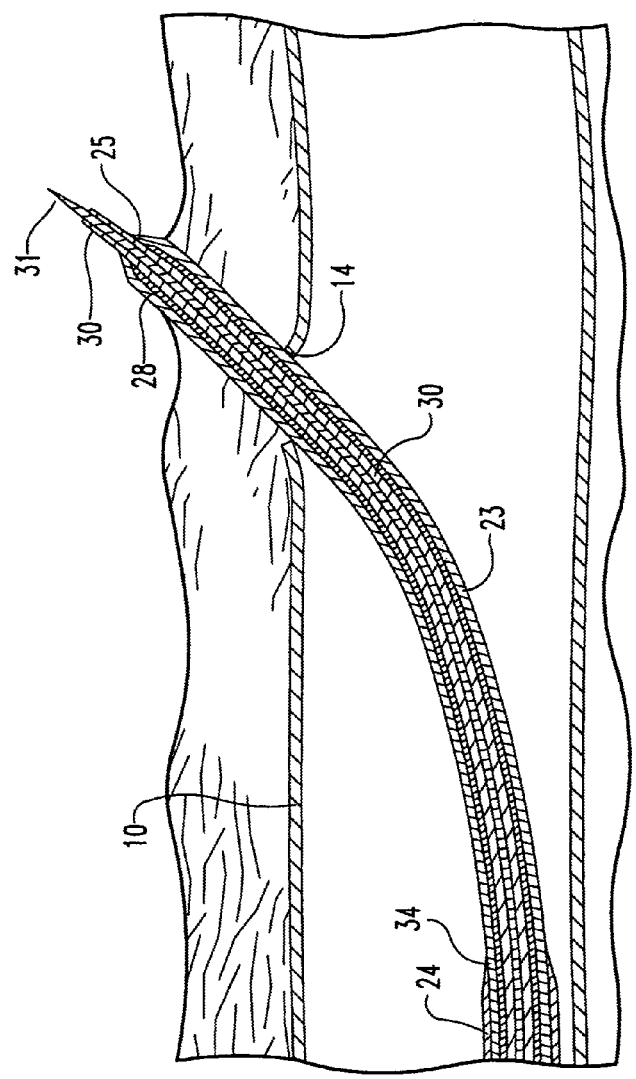
FIG. 10 depicts an illustrative deployment method of the present invention.
Figure 11:
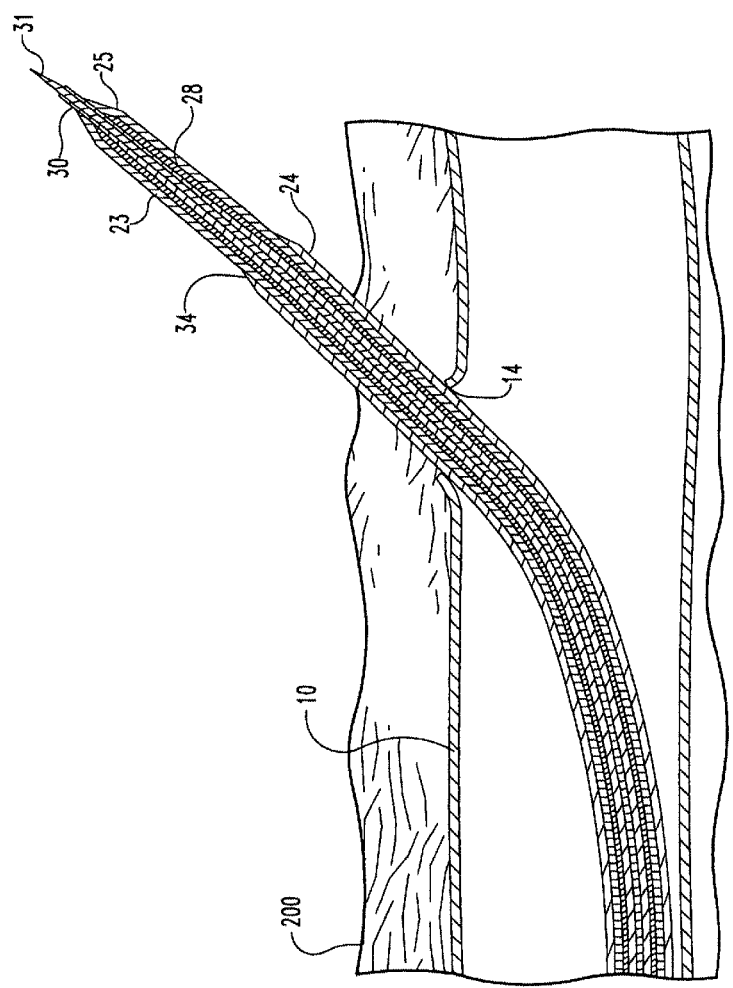
FIG. 11 depicts an illustrative deployment method of the present invention.

With reference now to FIG. 8, a guide catheter 30 and long needle 31 are threaded through the interior of stiffening cannula 28, and needle 31 is used to penetrate the wall of greater saphenous vein 10 as illustrated. Needle 31 is advanced through the adjacent tissue toward the surface of the skin. In certain embodiments of the invention, needle 31 has a needle point of such a sharpness that the needle does not exit the skin, but rather creates a visible bump 32 in the skin from which the location of the needle 31 can be visibly discerned. The skin can be nicked at or near the apex of the bump 32 with a scalpel or other suitable instrument, to allow exit of the needle 31, as illustrated in FIG. 9. Subsequently, needle 31 is grasped with forceps or any other suitable means and used to pull deployment assembly 21 through the skin with guide sheath 23 and elements internal thereof exiting first, during which tapered end 25 serves as a dilator to ease exit (see FIG. 10), and eventually exposing end 34 of delivery sheath 24 externally of the skin (see FIG. 11). Subsequently, all components except for delivery sheath 24 are withdrawn, leaving in place delivery sheath 24 with its internal cannula open 35 (see FIG. 12) for use in delivering an occlusion device, for example as described below.

Figure 12:
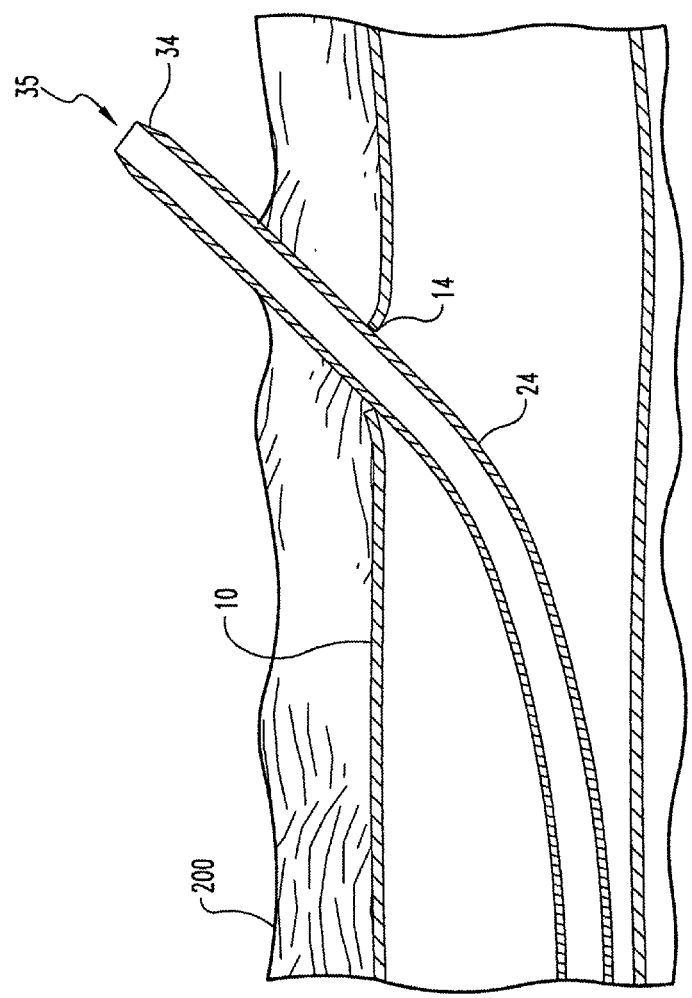
FIG. 12 depicts an illustrative deployment method of the present invention.
Figure 13:
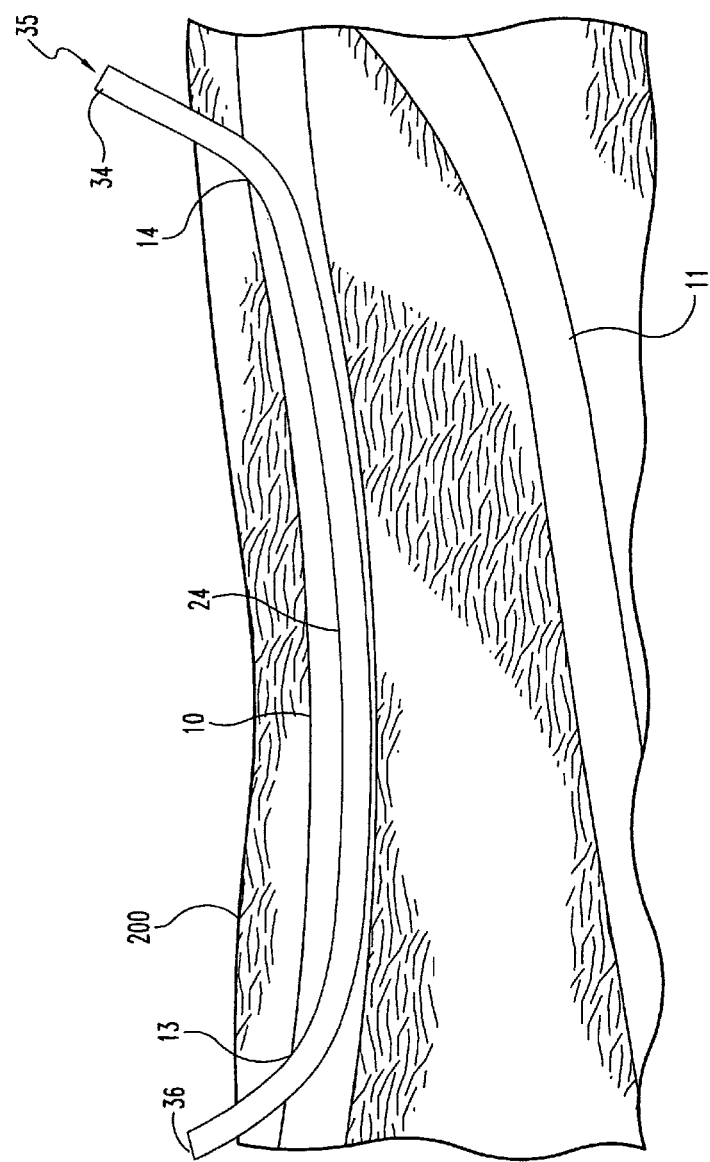
FIG. 13 depicts an illustrative deployment embodiment of the invention in that portion of the human leg occurring generally between points 13 and 14 in FIG. 1.

With reference now to FIG. 13 shown is a diagram including greater saphenous vein 10 from points 13-14, at the same stage of the procedure as that shown in FIG. 12. Delivery sheath 24 is in place in a through-and-through fashion, having a first end 34 exposed through the skin at point 14 occurring near the groin of the patient adjacent the sapheno-femoral junction, and a second end 36 exposed through the skin adjacent the medial portion of the knee of the patient. In this fashion, internal cannula 35 of delivery sheath 24 is open and available for use in delivering a vascular occlusion device.

Figure 14:
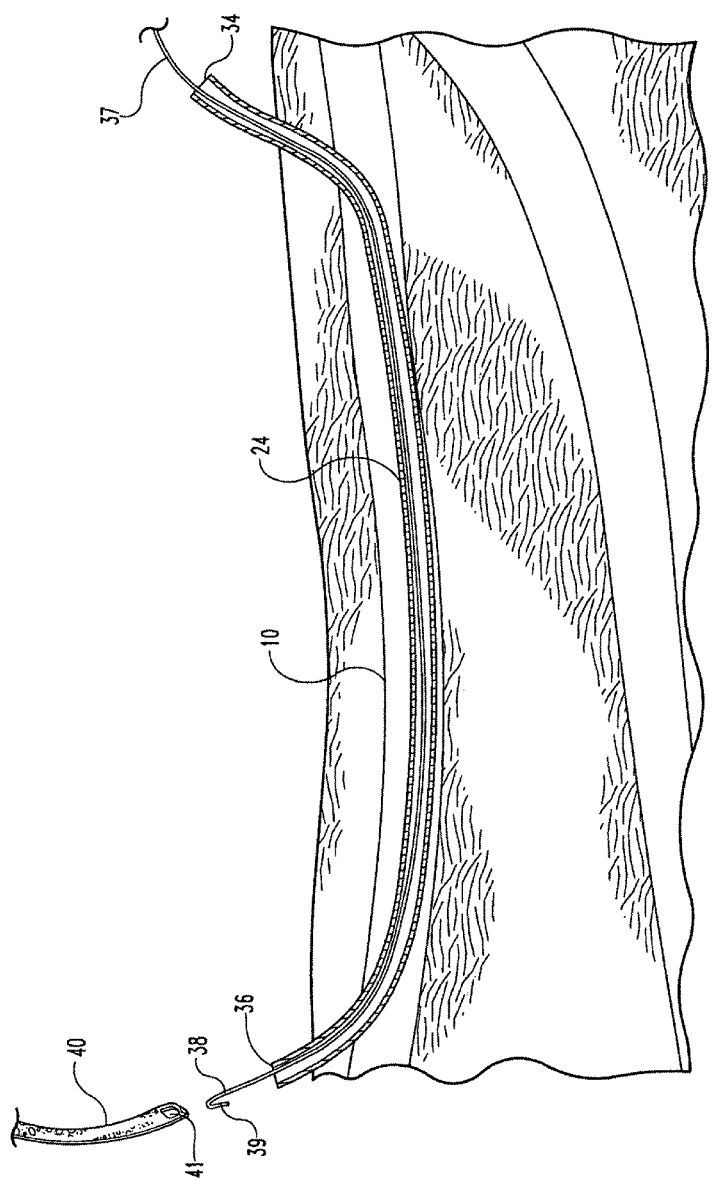
FIG. 14 depicts an illustrative deployment embodiment of the invention in that portion of the human leg occurring generally between points 13 and 14 in FIG. 1.
Figure 15:
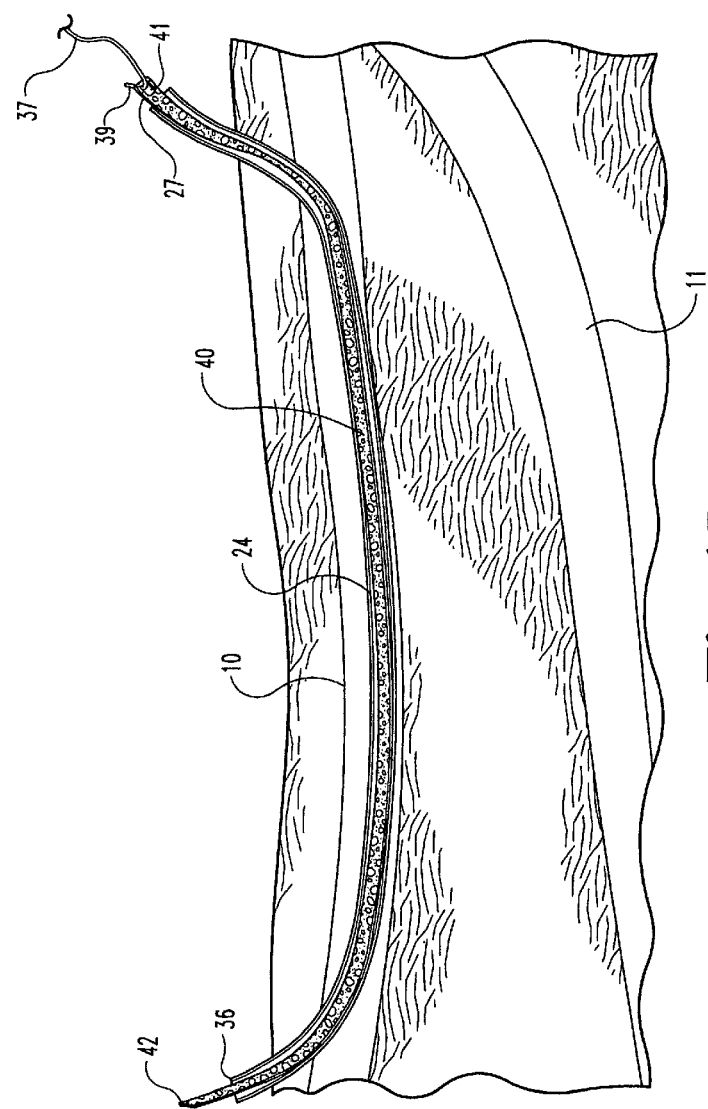
FIG. 15 depicts an illustrative deployment embodiment of the invention in that portion of the human leg occurring generally between points 13 and 14 in FIG. 1.
Figure 16:
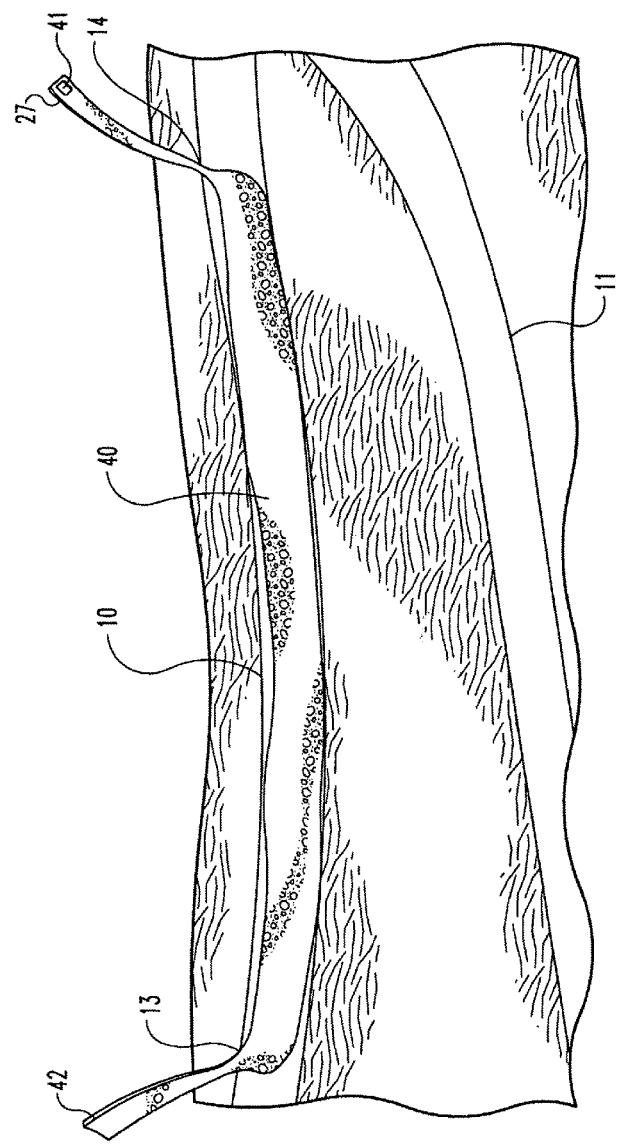
FIG. 16 depicts an inventive vascular occlusion device in an illustrative deployment embodiment of the invention.

Referring now to FIG. 14, in one embodiment, a relatively stiff guide wire 37 can be threaded through delivery sheath 24. Guide wire 37 has an engaging end 38 including a hooked portion 39 or other suitable adaptation for connection to occlusion device 40. Occlusion device 40 includes a looped structure 41 or any other suitable connection structure at an end thereof. Hooked portion 39 can be connected to looped structure 41, and guide wire 37 can thereafter be used to draw occlusion device 40 through delivery sheath 24, as generally shown in FIG. 15. In particular, FIG. 15 illustrates occlusion device 40 having been drawn through delivery sheath 24 to expose an end 27 adjacent looped structure 41 from the skin near the groin of the patient, leaving an end 42 exposed through the skin near the knee of the patient. After this, delivery sheath 24 can be withdrawn, leaving in place only occlusion device 40 in a through-and-through condition with the first end 27 and the second end 42 remaining external of the skin of the patient (see FIG. 16). Subsequently, the ends of the occlusion device 40 can be trimmed, and any excess length of device 40 remaining external of the patient can be tucked underneath the skin. The percutaneous access and exit sites can be closed by suturing or any other suitable technique, if necessary.

In some cases, it may be desirable to place more than one occlusion device 40 within the greater saphenous vein 10 of the patient. With reference again to FIGS. 14-15, if such is desired, more than one guide wire 37 may be passed through delivery sheath 24 to pull through a corresponding number of devices 40, or alternatively, sequential passes can be made of one or more guide wires 37 in order to pull additional devices 40 through the sheath. On the other hand, if sheath 24 has insufficient internal diameter to accommodate more than one device 40 at a time, again referring to FIG. 15, at this stage, a second guide wire 37 can be threaded through sheath such that guide wire 37 and device 40 are both received through sheath 24. Sheath 24 can then be withdrawn, leaving in place device 40 and guide wire 37 each in a through-and-through condition. The remaining guide wire 37 can then be used to guide a subsequent deployment assembly 21, and the overall procedure repeated one or more times as described above to place a second device 40, a third device 40, etc.

Upon being positioned within greater saphenous vein 10, occlusion device 40 or devices 40 restrict blood flow in the greater saphenous vein 10 so as to occlude or exclude the same. It is desired that occlusion device 40 be of such a dimension that the material comprising device 40 substantially blocks the internal lumen of greater saphenous vein 10. To this end, the device 40 can have a compressed condition and be adapted to convert to an altered physical configuration after deployment. For example, all or a portion of device 40 may be adapted to expand, unfold, unroll, untwist, harden, or otherwise progress to a condition other than that which it had during deployment and which aids in occluding the vessel. Alternatively or in addition, occlusion device 40 can cause localized thrombus to cause or assist in occluding the lumen of greater saphenous vein 10. Illustrative such expandable occlusion devices can comprise a porous sponge extracellular matrix (ECM) structure and/or a collagenous foam. For additional information concerning suitable sponge matrix materials and their preparation, reference can be made, for example, to U.S. Pat. No. 6,666,892 and International Publication No. WO03/002168, each of which is hereby incorporated herein by reference in its entirety.

Figure 17:
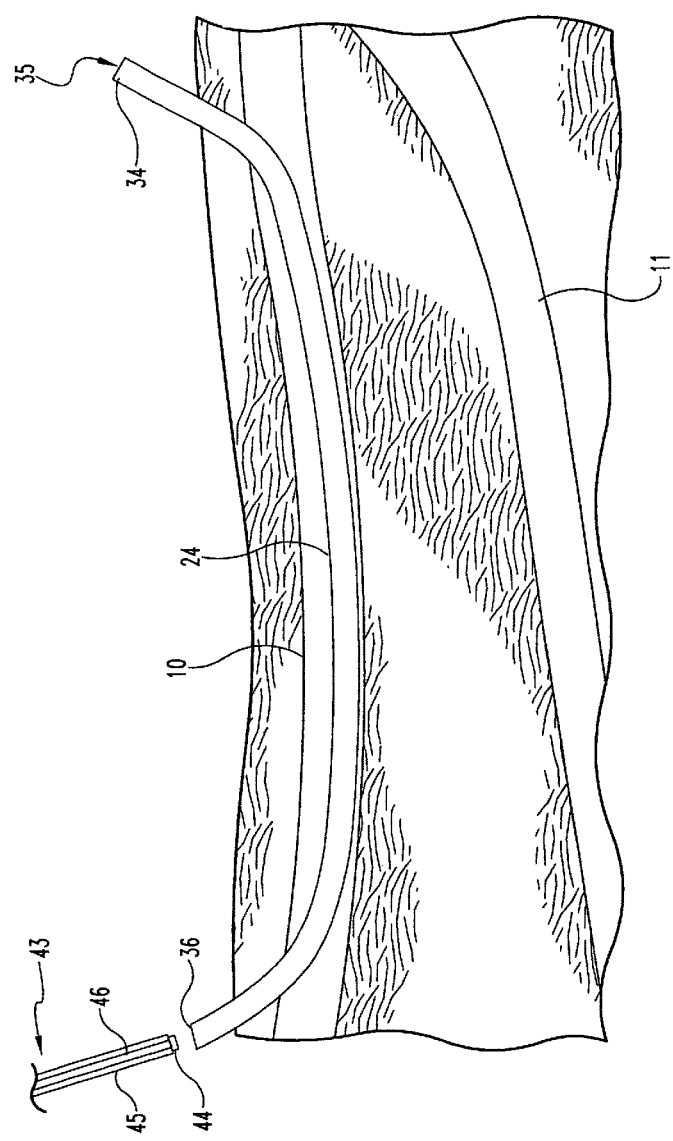
FIG. 17 depicts an illustrative deployment embodiment of the invention in that portion of the human leg occurring generally between points 13 and 14 in FIG. 1.

With reference now to FIG. 17, shown is another view similar to that depicted in FIG. 14, except illustrating an alternative technique for delivering an occlusion device. Occlusion assembly 43 includes occlusion device 44 received within an external cannula such as a sheath 45, for coaxial style delivery through delivery sheath 24. For these purposes, illustratively, sheath 24 can be a 12 French sheath and sheath 45 can be a 10 French sheath. Sheath 45 or other external cannula desirably has an elongate slit 46 therein or another opening or openings along its length. Such opening or openings are beneficial, for example, in that the device 44 can be sterilized after loading within the sheath 45 using gaseous agents such as ethylene oxide (EO) which penetrate through the opening or openings to contact and sterilize device 44. Procedurally, occlusion assembly 43 is threaded into and through delivery sheath 24 to achieve a through-and-through condition, whereafter sheaths 24 and 45 are withdrawn leaving occlusion device 44 in place in a through-and-through condition as generally described above. Device 44 can then be trimmed and tucked, and the procedure completed as generally described above.

Figure 18:
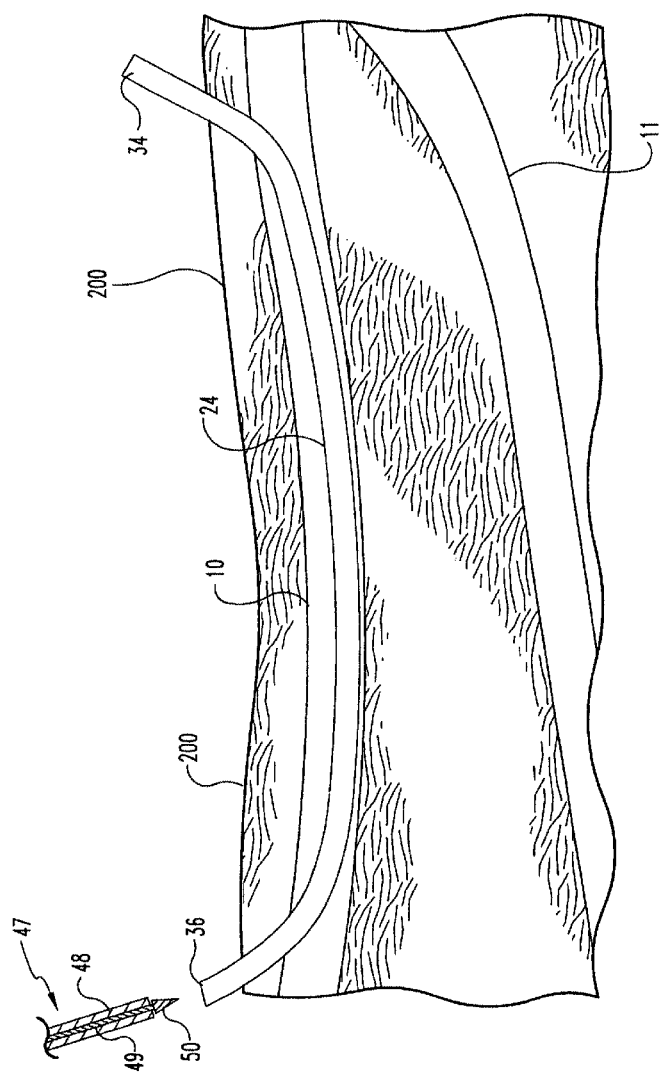
FIG. 18 depicts an illustrative deployment embodiment of the invention in that portion of the human leg occurring generally between points 13 and 14 in FIG. 1.
Figure 19A:
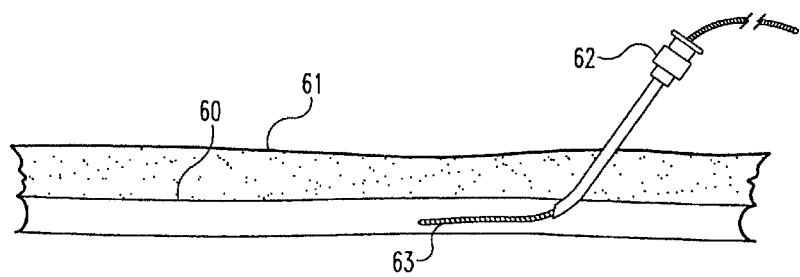
FIGS. 19A-19H depict an illustrative deployment embodiment of the invention.
Figure 19B:
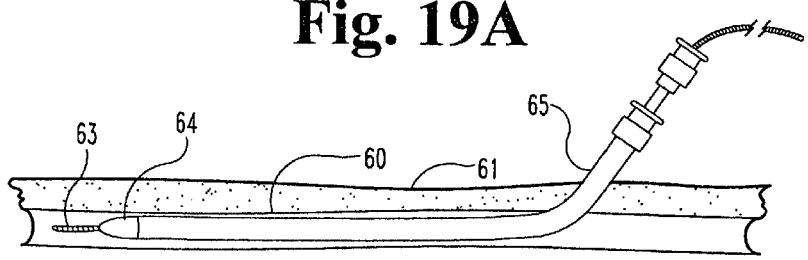
Figure 19C:
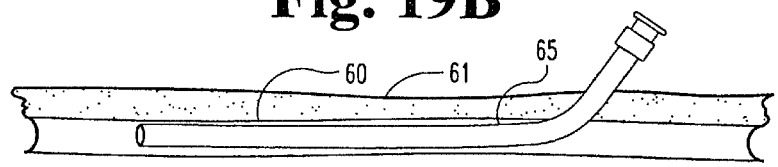
Figure 19D:
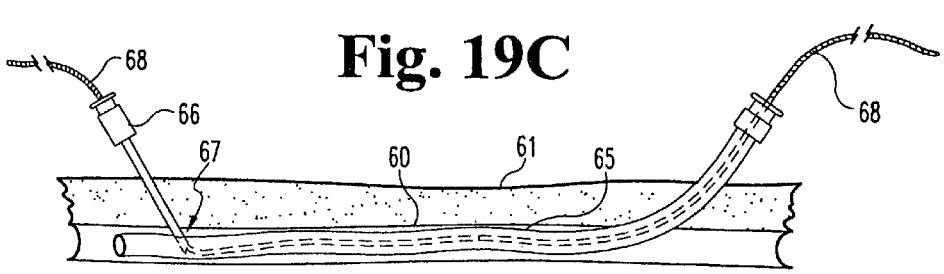
Figure 19E:
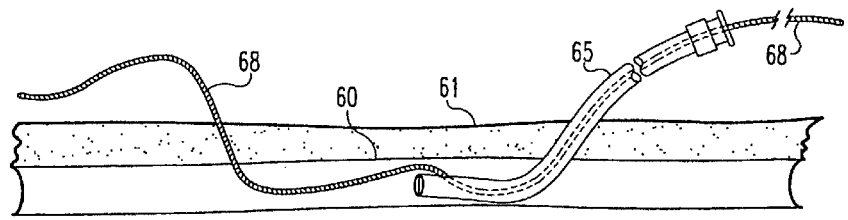
Figure 19F:
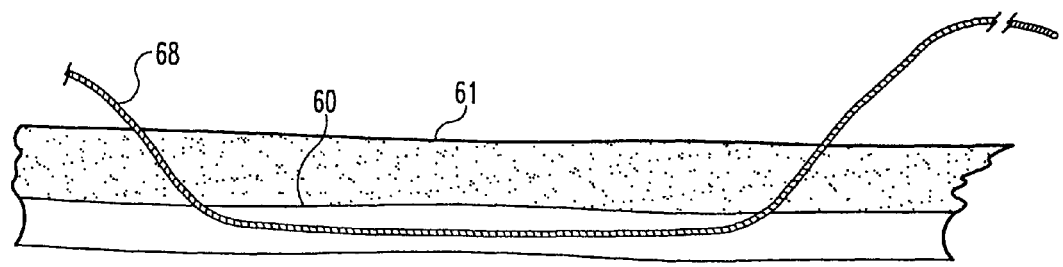
Figure 19G:
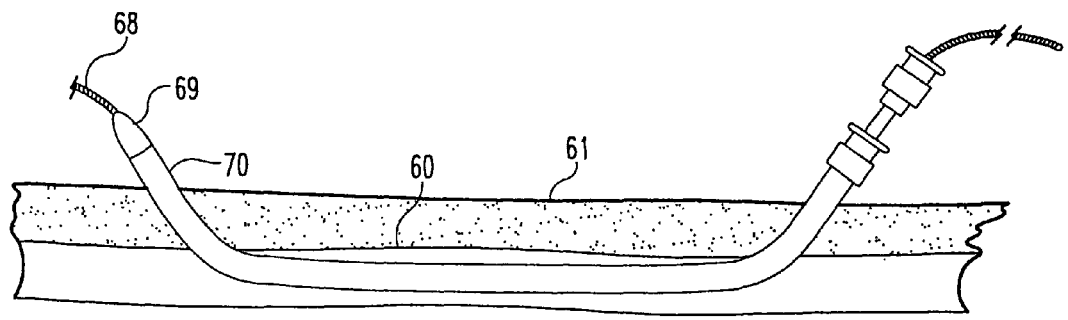
Figure 19H:
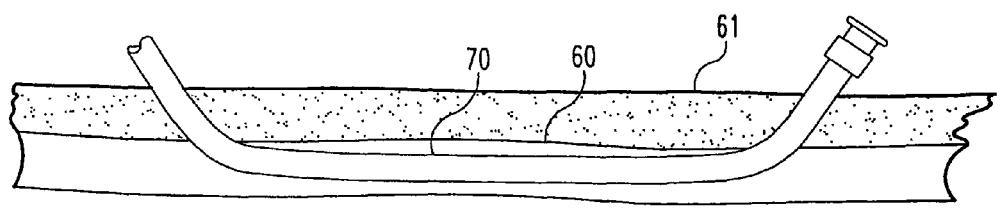

With reference now to FIG. 18, shown is a view similar to that depicted in FIG. 14, except showing an alternative occlusion device and delivery system. Particularly, delivery sheath 24 is in place in a through-and-through condition. An occlusion assembly 47 includes an elongate occlusion device 48 received concentrically around an internal guide member 49, such as a guide wire, and if desired is provided with an end piece 50 with a tapered end to assist in traversal of the occlusion device 48 through the delivery sheath 24. The assembly 47 including occlusion device 48, guide member 49, and end piece 50 has sufficient column strength and integrity to be pushed through delivery sheath 24 from end 36 to end 34, leaving occlusion device 48 in a through-and-through condition. Internal guide member 49 with end piece 50 and sheath 24 can then be withdrawn, and the occlusion device 48 trimmed and tucked prior to completing the procedure as described above.

With reference to FIGS. 19 and 20, illustrated are alternative methods for delivering occlusion devices by through-and-through percutaneous procedures. Taking first FIG. 19, FIG. 19A illustrates initial access to a vascular vessel 60 through the skin 61 via introducer needle 62, which is used to deliver guide wire 63 to the vessel 60. Guide wire 63 is used to guide an assembly including a dilator 64 and an outer sheath 65 into the vessel 60, as shown in FIG. 19B. The guide wire 63 and dilator 64 are withdrawn, leaving in place sheath 65 as shown in FIG. 19C. FIG. 19D shows a stage of the procedure in which a second percutaneous access is provided via introducer needle 66, with the needle 66 penetrating sheath 65. A guide wire 68 is introduced through needle 66 and traverses sheath 65 thus exiting the initial percutaneous access site. As shown in FIG. 19E, sheath 65 is withdrawn over guide wire 68 leaving in place guide wire 68 in a through-and-through condition as shown in FIG. 19F. An assembly including dilator 69 and sheath 70 is then introduced over guide wire 68 as shown in FIG. 19G, and the dilator 69 and guide wire 68 are withdrawn thereby leaving in place sheath 70 in a through-and-through condition as shown in FIG. 19H. Sheath 70 can then be used for the introduction of an occlusion device in a suitable manner including those described hereinabove.

Figure 20A:
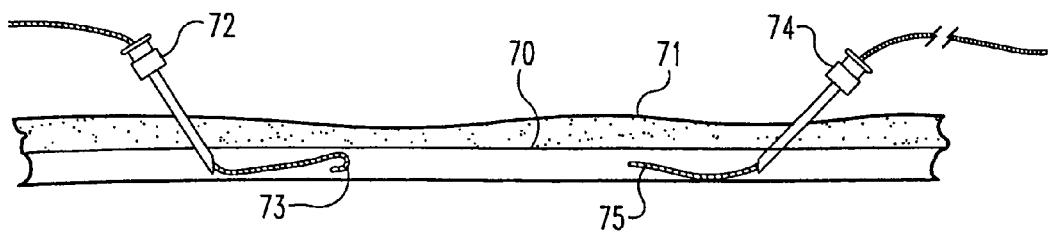
FIGS. 20A-20E depict an illustrative deployment embodiment of the invention.
Figure 20B:
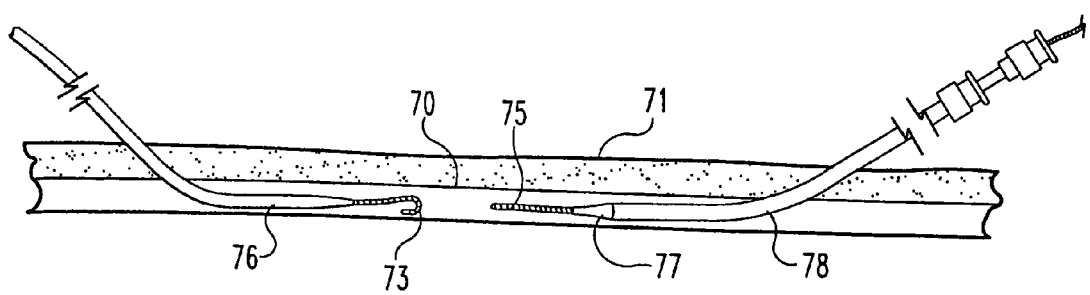
Figure 20C:
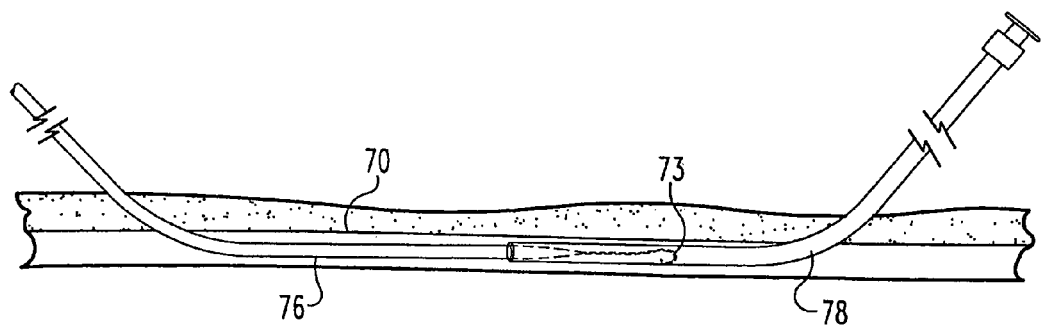
Figure 20D:
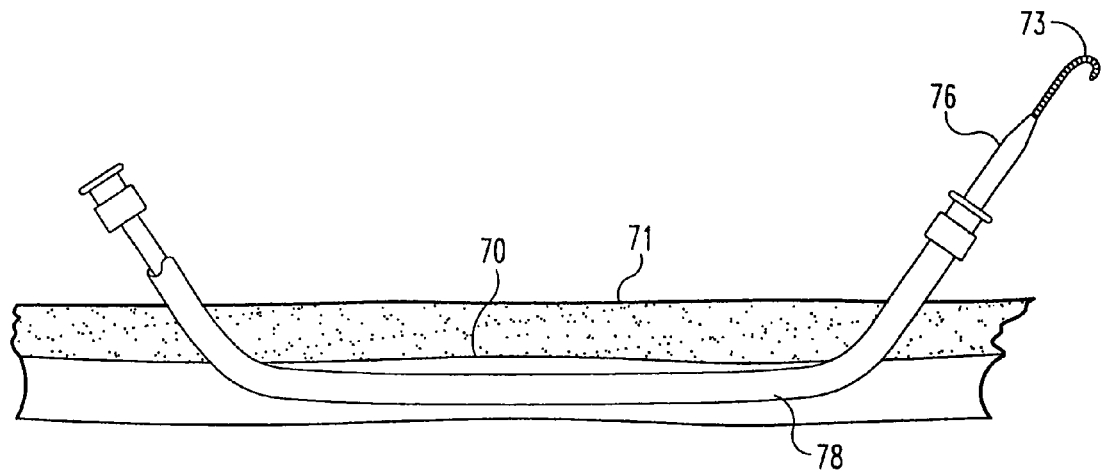
Figure 20E:
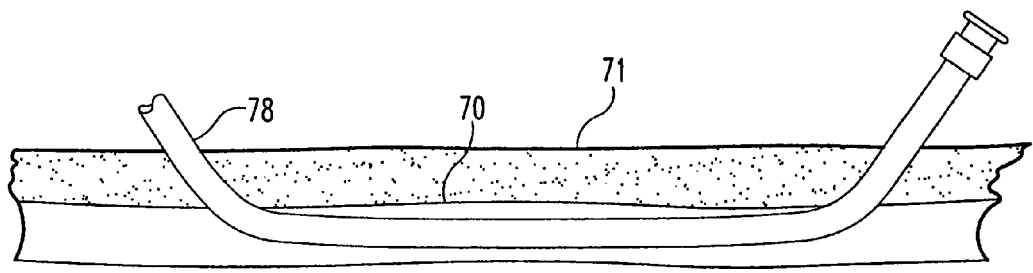

With reference now to FIGS. 20A-20E, shown is an alternative procedure for establishing a through-and-through sheath for delivery of an occlusion device. FIG. 20A illustrates an early stage in the procedure wherein access to vascular vessel 70 is provided through skin 71 at two locations. At a first location, introducer needle 72 accesses vessel 70 and is used to deliver a "J" guide wire 73 into vessel 70. At another location, introducer needle 74 is used to access vessel 70 and deliver guide wire 75 to vessel 70. As illustrated in FIG. 20B, a catheter 76 is advanced over the "J" guide wire 73, and an assembly including catheter 77 and overlying sheath 78 is advanced over guide wire 75. After introduction of the sheath 78 into vessel 70, guide wire 75 and catheter 77 are withdrawn from sheath 78. At this stage, as illustrated in FIG. 20C, "J" guide wire 73 and its accompanying catheter 76 are advanced into the cannula of sheath 78. Advancement is continued until catheter 76 and "J" guide wire 73 exit the opposite end of sheath 78 as shown in FIG. 20D. Catheter 76 can optionally have a segment (e.g. about 3 to 10 cm in length) proximal to the distal tip that tapers to a slightly enlarged external diameter. This segment would fit snugly into the sheath 78, and would create a transitioning external diameter that would ease exit of the sheath 78 from the second puncture site. FIG. 20E shows the sheath 78 thereafter established in a through-and-through condition after withdrawal of the catheter 76 and "J" guide wire 73 from the sheath 78. Sheath 78 can then be used for the deployment of an occlusion device in any suitable manner including those described above.

Although certain procedures have been described above for the delivery of occlusion devices, it will be understood that other modes of delivery of occlusion devices are also suitable in the present invention. For example, procedures involving only a single point of percutaneous access can be conducted, for instance wherein a delivery sheath is established through a percutaneous access site and into the vascular vessel to be occluded, and an occlusion device is delivered from the sheath using any suitable technique including pushing the occlusion device from the end of the sheath, e.g. as the sheath is withdrawn. In situations where needed, techniques and/or device adaptations can be employed to help to prevent withdrawal of the occlusion device as the sheath is being withdrawn from the patient over the occlusion device. These include for example the use of anchoring portions connected to the occlusion device that forcibly contact vessel walls and resist migration and/or local external compression (e.g. particularly in the case of shallow vessels) to collapse the vessel walls against a leading portion of the occlusion device exposed from the end of the sheath and/or fixing an end, or a portion of the body, of the occlusion device to the vasculature using a suitable securing means, such as one or more sutures or staples, to facilitate maintaining the position of the occluder device as the sheath is withdrawn.

As well, as a modification of a through-and-through percutaneous procedure, a single percutaneous access to a vein or other vessel through the skin can be provided, wherein at a spaced location of the accessed vessel, the vessel is again penetrated, but not the skin. One end of an elongate occlusion device can then be passed through the second penetration of the vessel and anchored in the surrounding tissue, and the percutaneous access site finished off as described above in connection with the through-and-through procedures. In the context of occluding the greater saphenous vein, such adaptations and/or techniques can be used with the percutaneous access site provided either at the knee level or near the groin in the area of the sapheno-femoral junction, or any appropriate location in between. As well, upon establishing a sheath containing a vascular occlusion device within a vessel to be occluded, a second vascular access sight can be provided near the end of the sheath, and a snare basket, or other suitable device for maintaining hold on the end of the vascular occlusion device, can be used to maintain the position of the occlusion device as its overlying sheath is withdrawn from the first percutaneous access site. Further, it is contemplated within certain embodiments of the invention that cut-down or other surgical procedures could be used in providing access to vascular vessels for delivery of vascular occlusion devices.

Figure 20F:
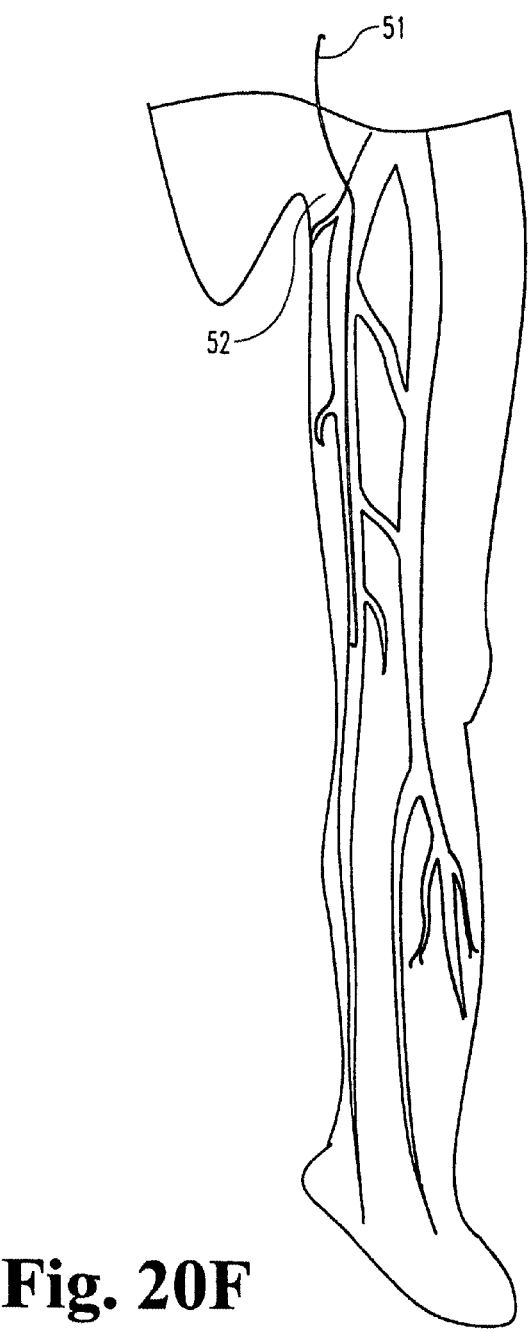
FIGS. 20F-20I depict an illustrative deployment embodiment of the invention.
Figure 20G:
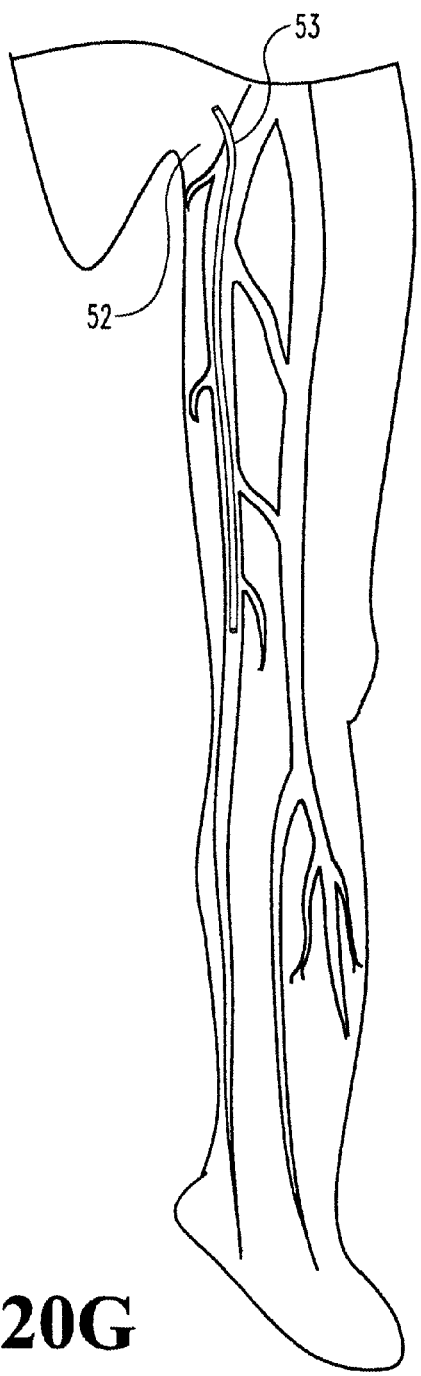
Figure 20H:
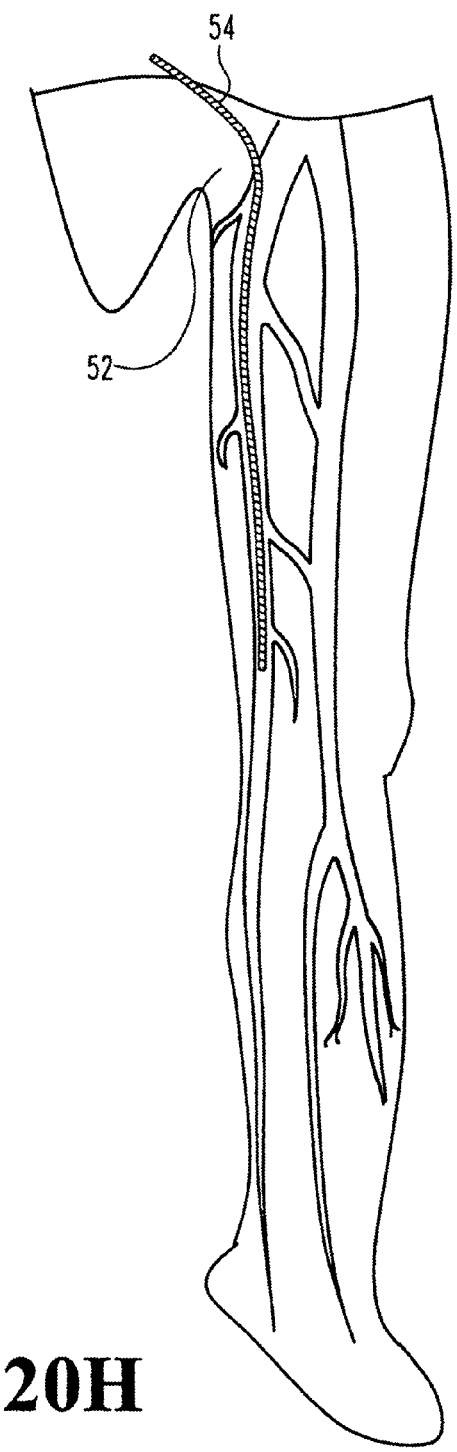
Figure 20I:
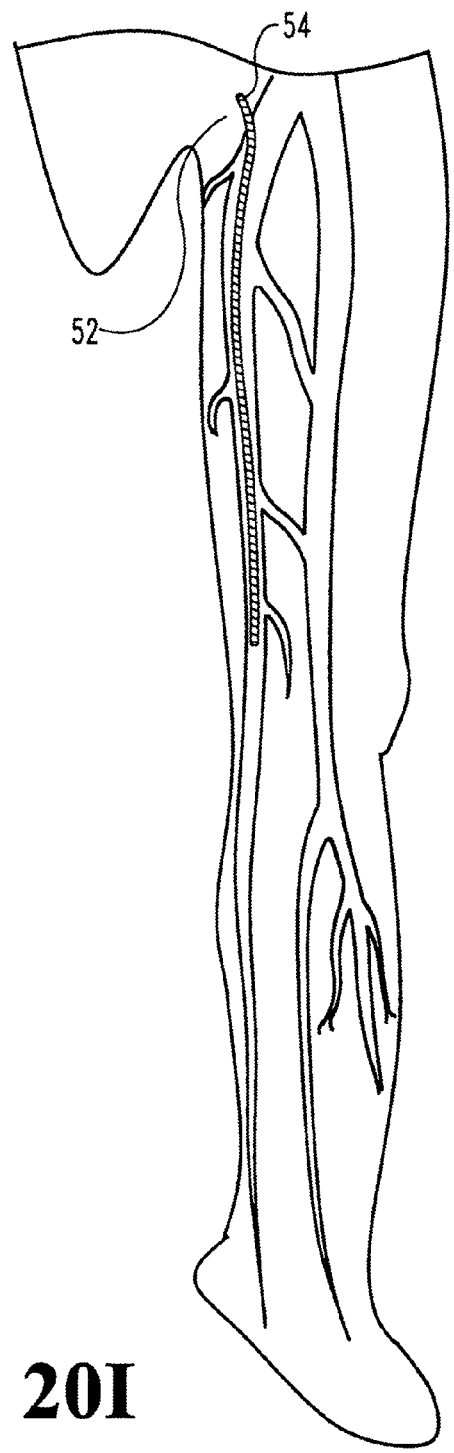
Figure 20J:
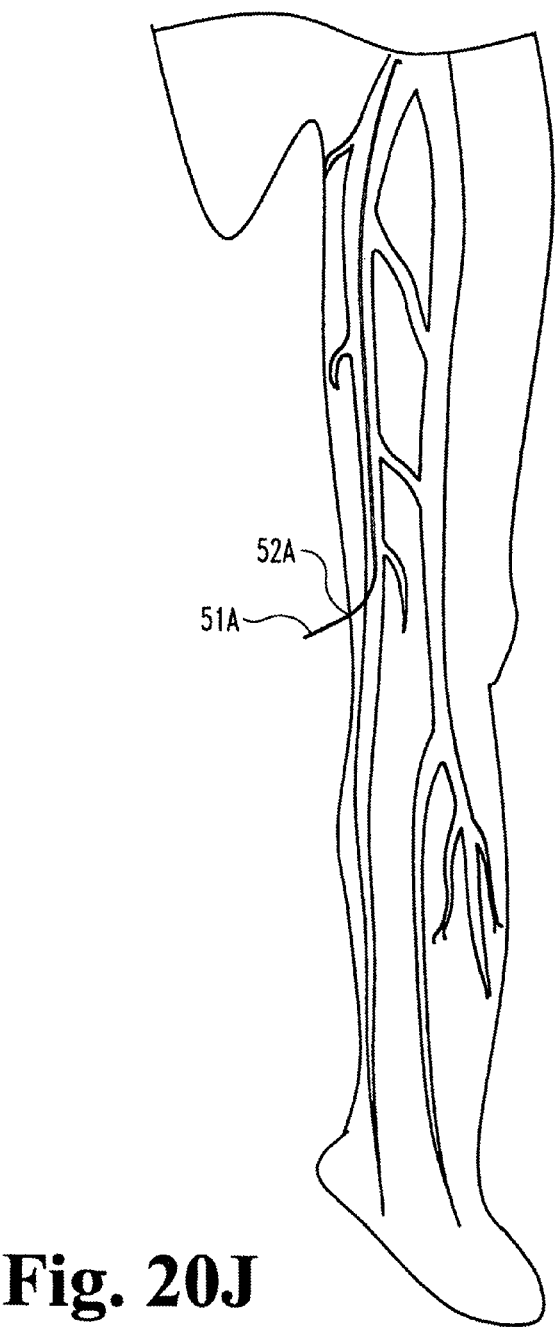
FIGS. 20J-20M depict an illustrative deployment embodiment of the invention.
Figure 20K:
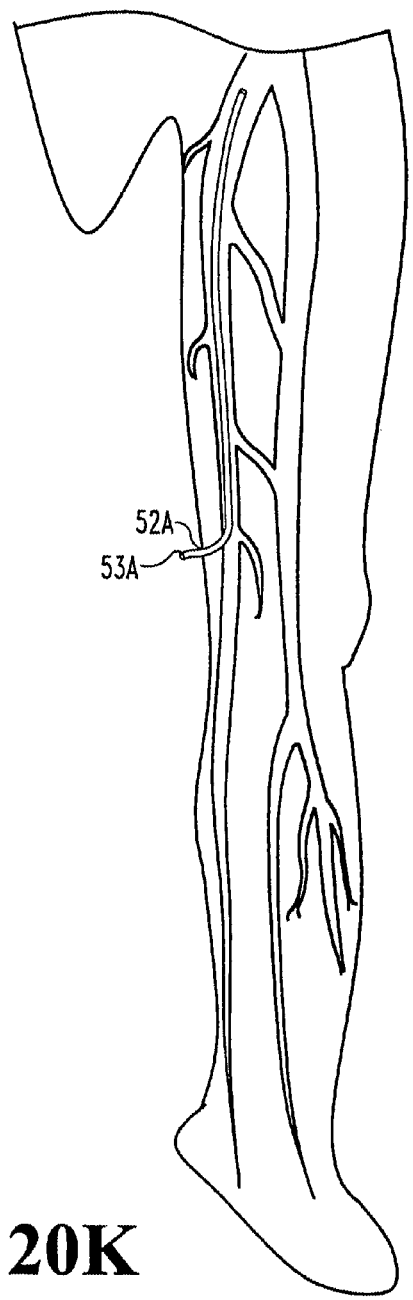
Figure 20L:
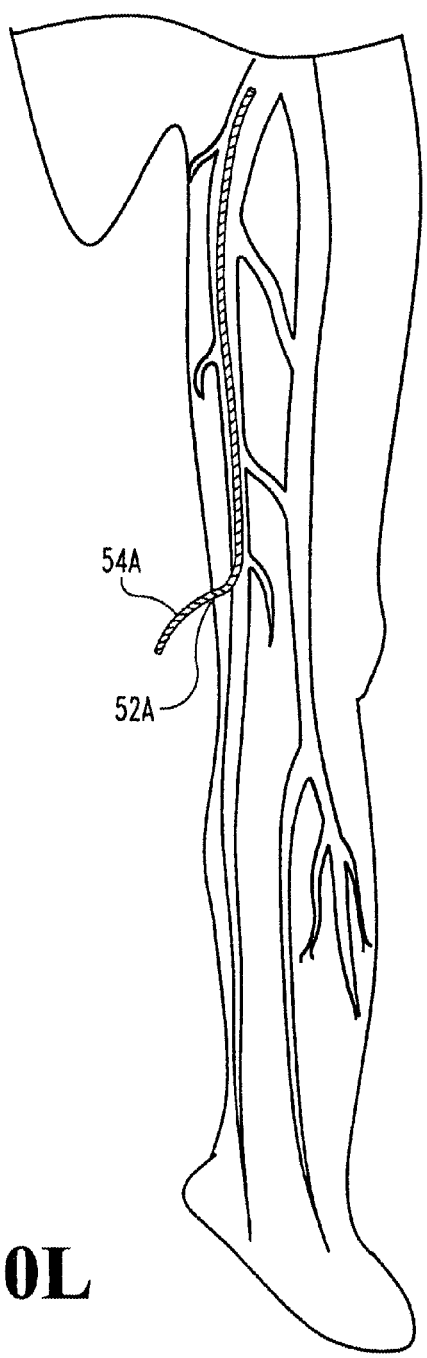
Figure 20M:
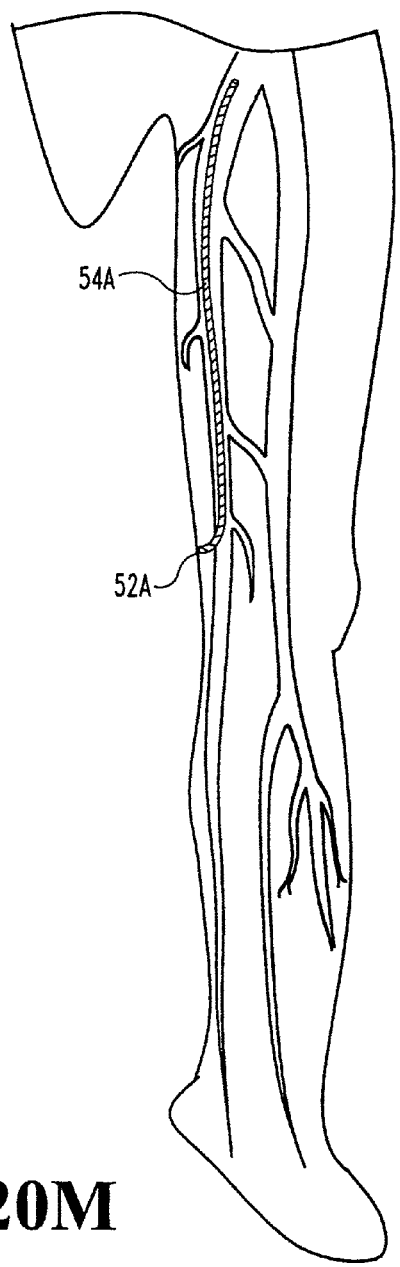

To illustrate further percutaneous delivery methods, shown in FIGS. 20F-20I is one descending delivery method involving only a single point of access. As shown in FIG. 20F, a guide wire 51 such as a J-wire is established in the greater saphenous vein via a percutaneous entry 52 near the groin. Subsequently, using the wire 51, a cannulated device 53 such as a catheter or sheath is established in the vein (FIG. 20G), and an occluder device 54 is delivered to the vein through the cannulated device 53 (FIG. 20H), e.g. by pushing or otherwise delivering the occluder device 54 out of the cannulated device 53 and withdrawing the cannulated device 53, potentially in a simultaneous operation. In one mode of practice, the occluder device 54 can have a length sufficient to extend from the vein and out of the percutanous exit 52, as shown in FIG. 20H. The occluder device can then be trimmed and if desired secured at the site of percutaneous entry 52 (FIG. 20I). FIGS. 20J-20M illustrate a similar one-site percutaneous delivery, except using an ascending approach with entry just above the knee.

Figure 20P:
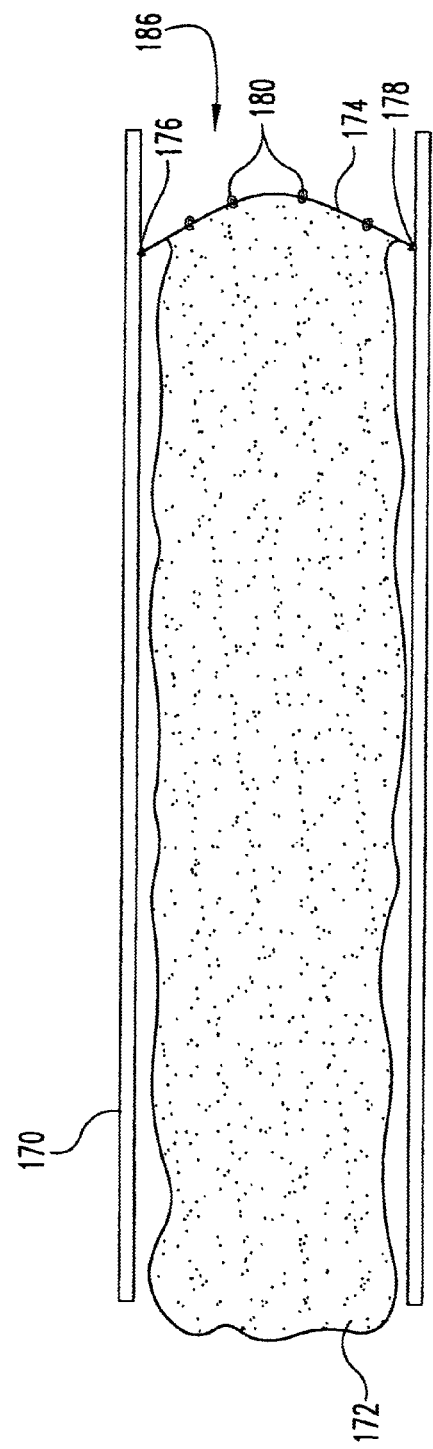

To illustrate yet further percutaneous delivery methods and occlusion devices, shown in FIGS. 20N-20P is an alternative occlusion device and delivery system utilizing a single point of access. In this embodiment, turning to FIG. 20N, the occlusion device 186 comprises a ribbon or band 172 attached to a fixation device 174, such as a flexible tube or rod, using one or more sutures 180, or other suitable securing means. Optionally, each end of the fixation device 176, 178 can terminate with one or more barbs, or other suitable anchoring means. The occlusion device 186 can be deployed by first locating a deployment sheath 182 in a vascular vessel 170. Next, the ribbon 172 portion of the occlusion device 186 can be loaded into a delivery sheath 184 while leaving the fixation device 174 external to the distal end 185 of the delivery sheath 184. Next, the delivery sheath 184, containing the occlusion device 186, can be placed inside the deployment sheath 182 in a manner that compresses or flexes the fixation device 174 and the delivery sheath 184 can be pushed through the deployment sheath 182. As the fixation device 174 breaches the distal end of the deployment sheath 183, it will expand, thereby anchoring itself into the wall of the vessel 170 (see FIG. 20O). After the fixation device 174 anchors, the deployment sheath 182 and delivery sheath 184 can be retracted to deploy the ribbon 172 into the vessel (see FIG. 20P). Alternatively, a plurality of occlusion devices 186 can be deployed in the same vascular vessel 170 according to the above method to achieve suitable occlusion and/or thrombosis of the vascular vessel 170. Still alternatively, the ribbon 172 can be folded over and secured to the fixation device 174, thereby forming two legs or bands for achieving occlusion.

Figure 21:
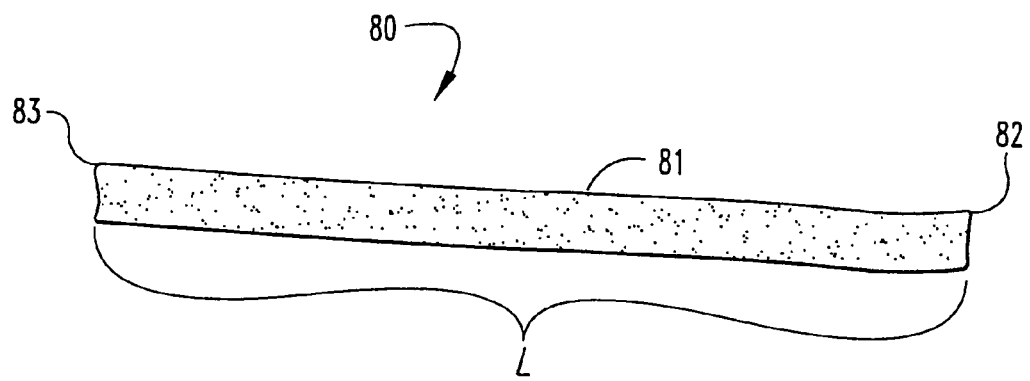
FIG. 21 depicts an illustrative occlusion device of the invention.

FIGS. 21 to 35B illustrate various embodiments of vascular occlusion devices of and for use in the invention. FIG. 21 shows vascular occlusion device 80 having an occlusion body 81, and first end 82, and a second end 83. Device 80 has a length "L" sufficient to occlude the length of the passage for which occlusion or ablation is desired. In accordance with certain embodiments of the invention, the device 80 will have a length sufficient and will be positioned so as to traverse at least one vessel that branches from the vessel to be occluded, for instance a perforator or communicator vein branching from a larger vein to be occluded such as a saphenous vein, e.g. the greater saphenous vein. In the context of greater saphenous vein occlusion procedures as described above, length "L" will be sufficient to traverse the greater saphenous vein from position 13 to position 14, desirably having sufficient excess length to exit percutaneous access sites at those locations for processing as described. These same considerations may be applied to the other vascular occlusion devices described herein.

Figure 22:
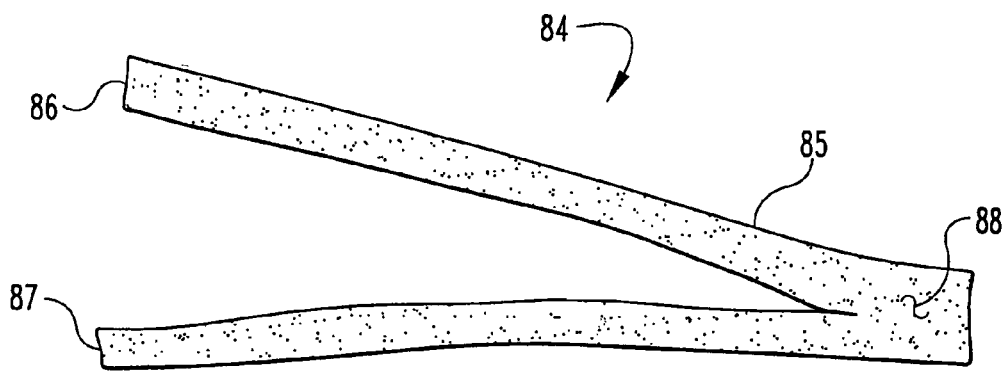
FIG. 22 depicts an illustrative occlusion device of the invention.

FIG. 22 shows occlusion device 84 having an occlusion body 85, with first and second ribbons 86 and 87 of occlusion material. Ribbons 86 and 87 are adjoined to one another integrally by an area 88 of occlusion material.

Figure 23:
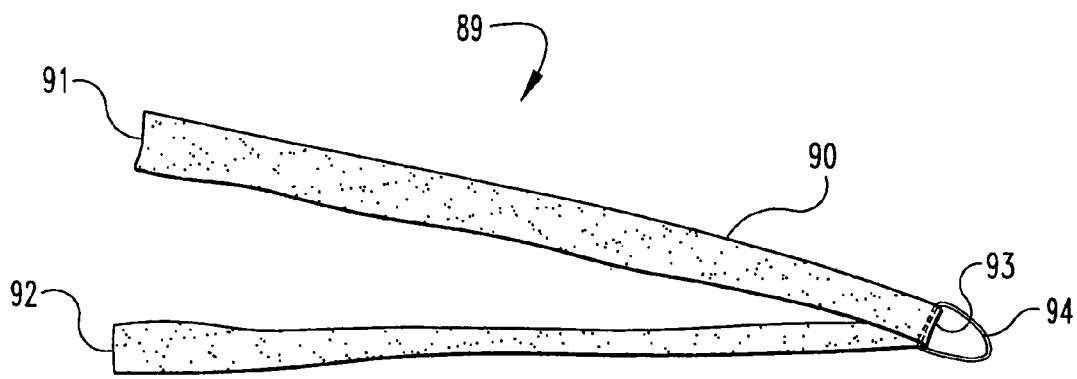
FIG. 23 depicts an illustrative occlusion device of the invention.

FIG. 23 shows occlusion device 89 having an occlusion body 90 with first and second legs or ribbons of material 91 and 92. Ribbons 91 and 92 are formed by creating a fold 93 in an integral longer sheet of material. If desired, a wire loop 94 or any other suitable tethering adaptation can be positioned around fold 93 or otherwise connected to the occlusion body 90.

Figure 24:
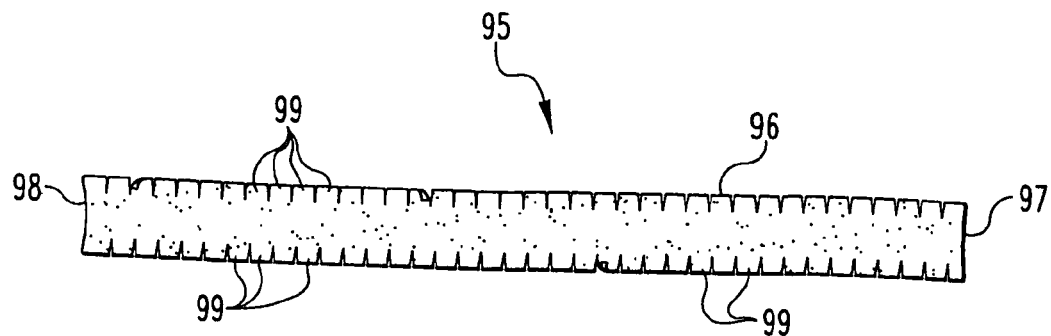
FIG. 24 depicts an illustrative occlusion device of the invention.

Illustrated in FIG. 24 is an occlusion device 95 having occlusion body 96 with a first end 97 and a second end 98 thereof. Occlusion body 96 includes a plurality of cuts or slits along the length thereof to form flares or legs 99 which increase the surface area for contact with blood after deployment and enhance the occlusive character of the device 95, e.g. by promoting thrombus.

Figure 25:
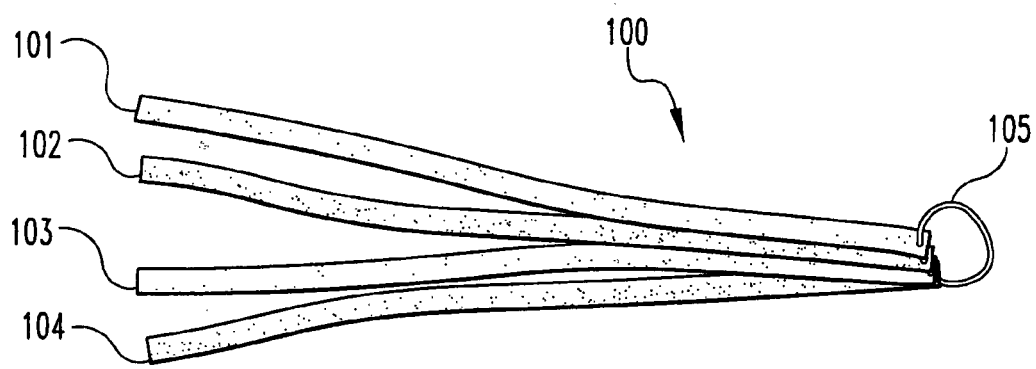
FIG. 25 depicts an illustrative occlusion device of the invention.

FIG. 25 shows occlusion device 100 having a plurality of ribbons 101, 102, 103, and 104 connected by an element 105 such as a wire loop threaded through ends of the ribbons.

Figure 26:
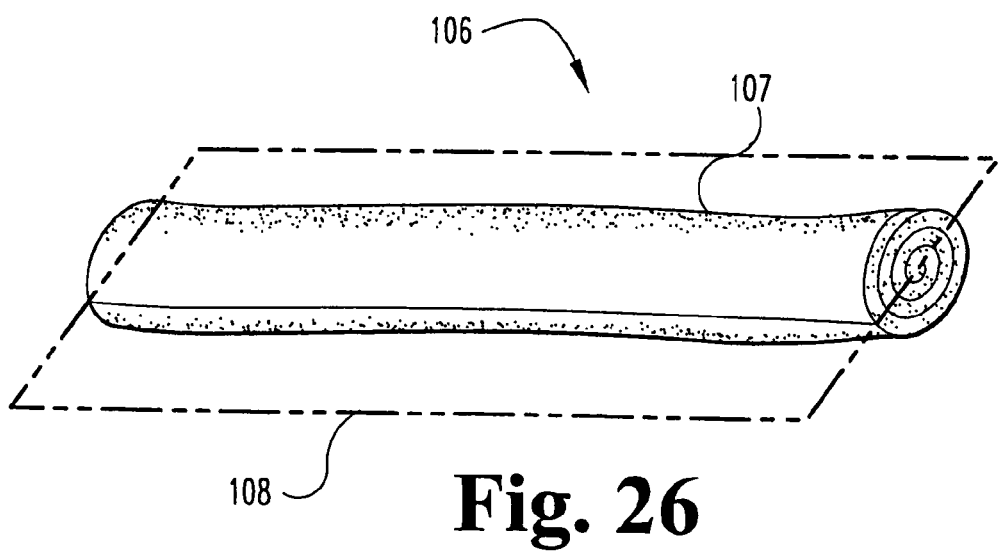
FIG. 26 depicts an illustrative occlusion device of the invention.

Shown in FIG. 26 is occlusion device 106 formed as a roll of occlusion material to provide a generally cylindrical occlusion body 107. Additionally, occlusion body 107 could be partially or completely slit along plane 108 and potentially additional planes, to provide modified configurations having increased surface area for blood contact.

Figure 27:
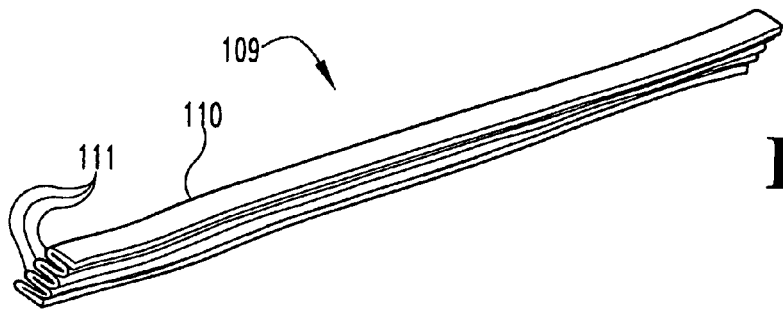
FIG. 27 depicts an illustrative occlusion device of the invention.

Referring now to FIG. 27, shown is occlusion device 109 having an occlusion body 110, formed by creating multiple folds 111 in a sheet of occlusion material. In this regard, it will be understood that this folded adaptation and other adaptations described herein can be designed to render the occlusion devices more compact and less voluminous for delivery, but which devices expand, unfold, or otherwise take on an increased dimension after delivery to facilitate the occlusion function.

Figure 28:
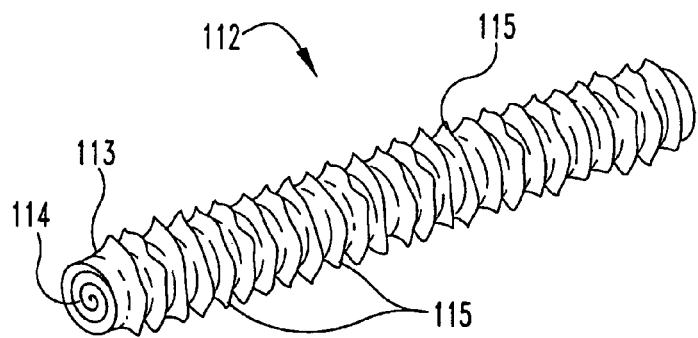
FIG. 28 depicts an illustrative occlusion device of the invention.

FIG. 28 shows an occlusion device 112 having an occlusion body 113 formed as a roll 114 of occlusion material. The external surface of occlusion body 113 has been contoured to create a plurality of bumps, flares or other protuberances 115 along the length thereof.

Figure 29A:
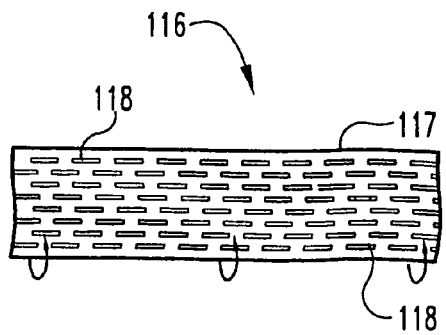
FIG. 29A depicts an illustrative occlusion device of the invention.
Figure 29B:
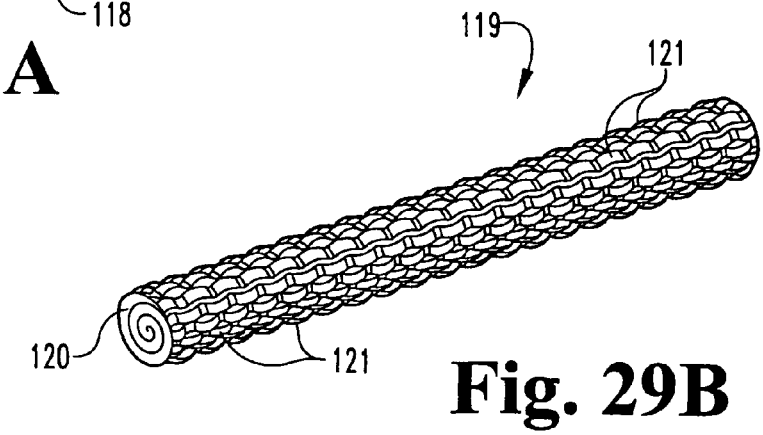
FIG. 29B depicts an illustrative occlusion device of the invention.

FIGS. 29A and 29B illustrate additional occlusion devices of the invention. FIG. 29A shows occlusion device 116 having an occlusion body 117 formed of an occlusion material. Body 117 includes a plurality of cuts or slits 118, for example to provide a mesh configuration, to increase surface area for blood contact. Additionally, occlusion body 117 can be rolled (see arrows) in order to form an alternate occlusion device 119 shown in FIG. 29B. Device 119 includes a generally cylindrical occlusion body 120 having irregular, raised loops or others portions of material 121 flaring from its surface.

Figure 30A:
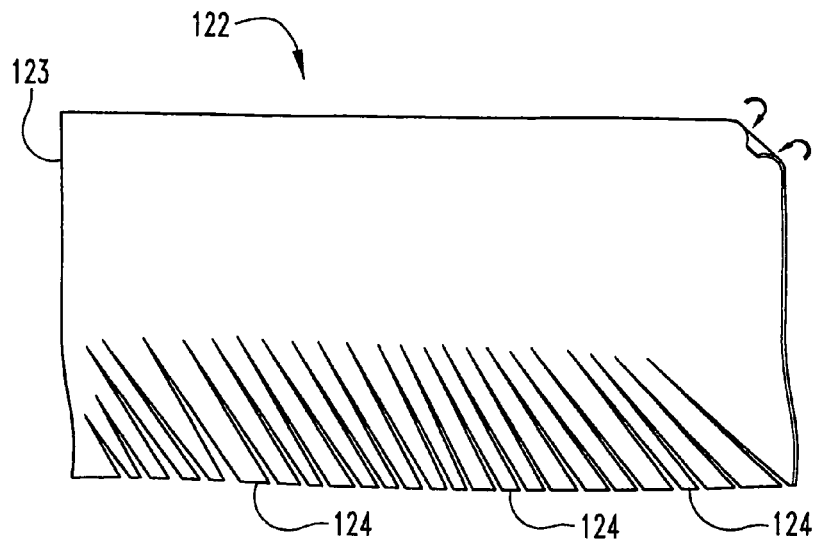
FIG. 30A depicts an illustrative occlusion device of the invention.
Figure 30B:
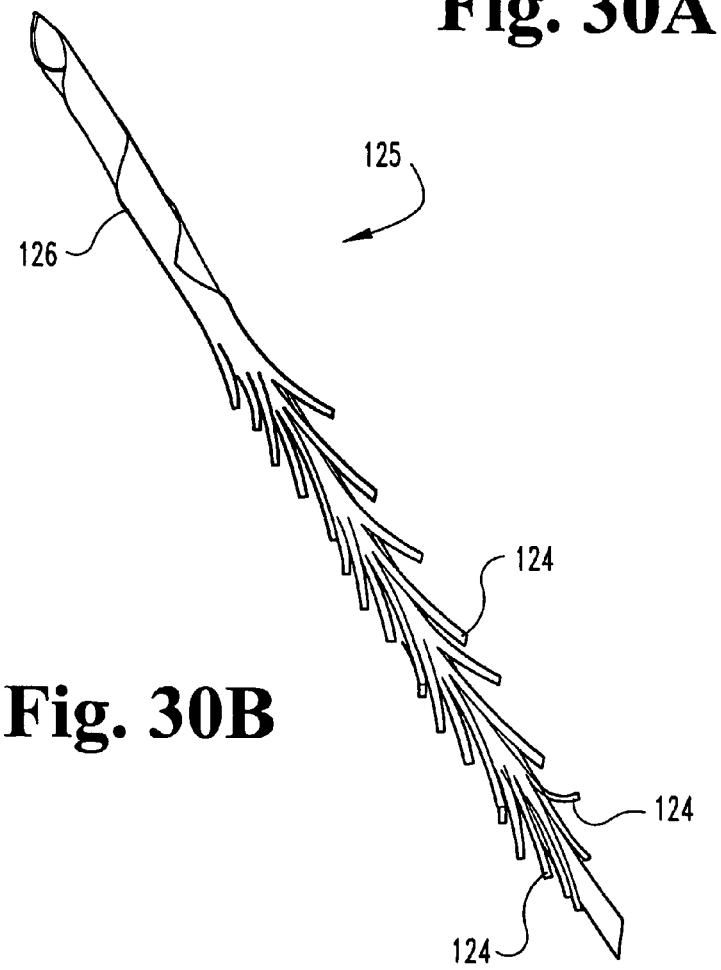
FIG. 30B depicts an illustrative occlusion device of the invention.

Additional embodiments of occlusion devices of the invention are shown in FIGS. 30A and 30B. FIG. 30A shows an occlusion device 122 including an occlusion body 123 having a plurality of legs or ribbons of material 124 established along an edge thereof by cutting or slitting material. If desired, occlusion body 123 can be rolled diagonally from a corner thereof (see arrows) in order to provide occlusion device 125 illustrated in FIG. 30B. Device 125 includes a generally cylindrical body 126 and in its rolled configuration ribbons 124 extend or flare from the surface thereof for increased blood contact.

Figure 31:
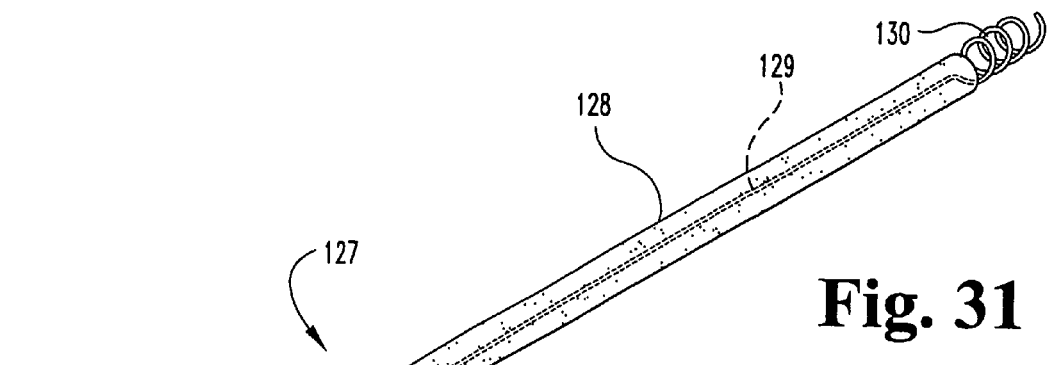
FIG. 31 depicts an illustrative occlusion device of the invention.

In other occlusion devices of the invention, it is contemplated that occlusion material in any suitable form, such as a ribbon, band, foam, cylinder, or the like, can be combined with elements for anchoring one or both ends of the occlusion device within a vascular vessel. Illustratively, shown in FIG. 31 is an occlusion device 127 having an occlusion body 128 made out of an occlusion material, and an elongate wire or other element 129 received within occlusion body 128. Wire or other element 129 exits the ends of the occlusion body 128, and provides coils 130 and 131 which can be configured to expand and provide points of securement of device 127 within a vascular vessel. As well, if desired, coils 130 and 131 may have synthetic fibers attached thereto to facilitate thrombus formation, for example as conventionally incorporated on commercial platinum or stainless steel embolization and occlusion coils. Further, while the occlusion body 128 is shown in tubular form, it can occupy any suitable shape or form, such as a ribbon, band, foam, or the like.

Figure 32:
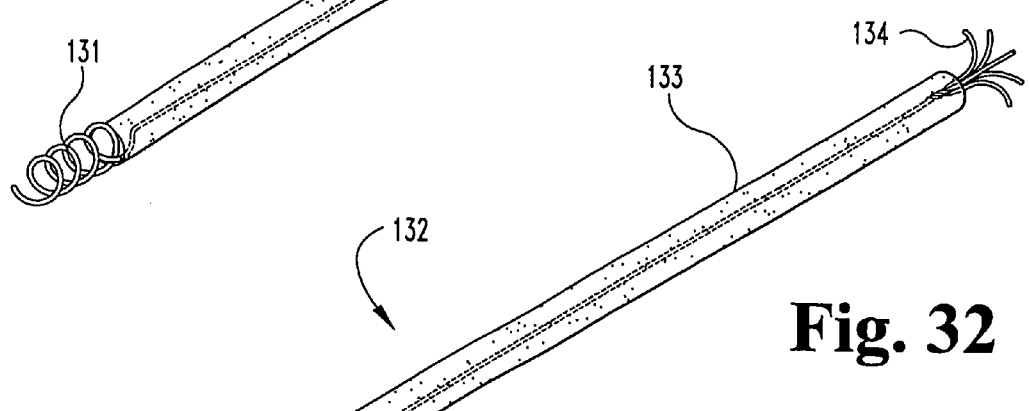
FIG. 32 depicts an illustrative occlusion device of the invention.

Shown in FIG. 32 is occlusion device 132 similar to that depicted in FIG. 31, including an occlusion body 133, and an internal wire or other element, and securement adaptations 134 and 135 provided by a plurality of diverging filaments or wire elements such as those found in vascular filters.

Figure 33:
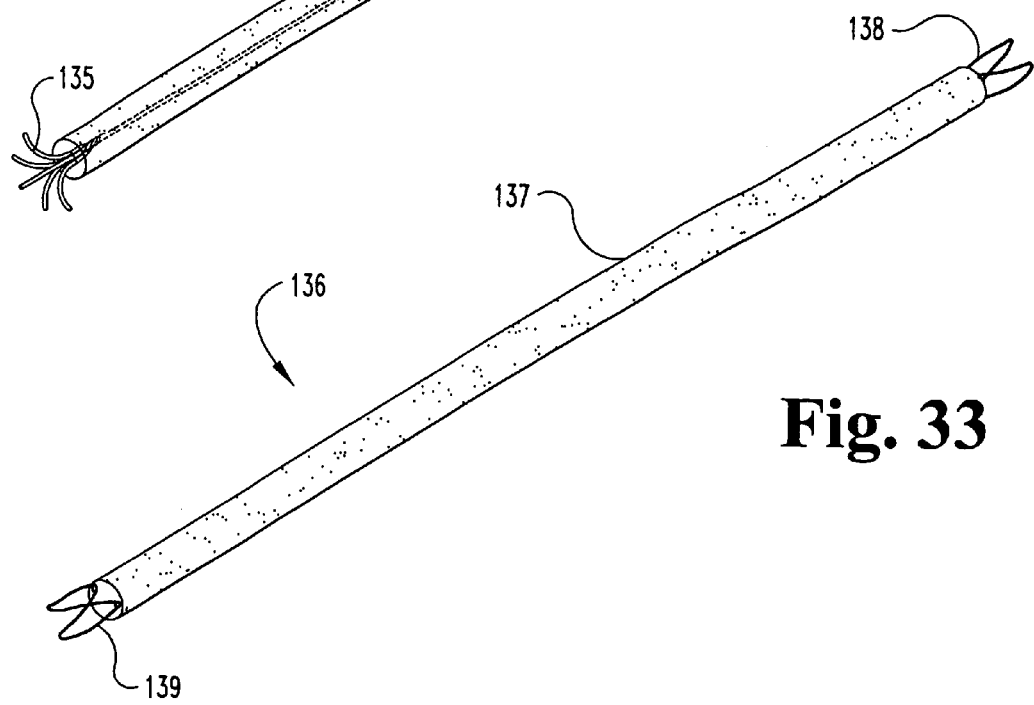
FIG. 33 depicts an illustrative occlusion device of the invention.
Figure 34:
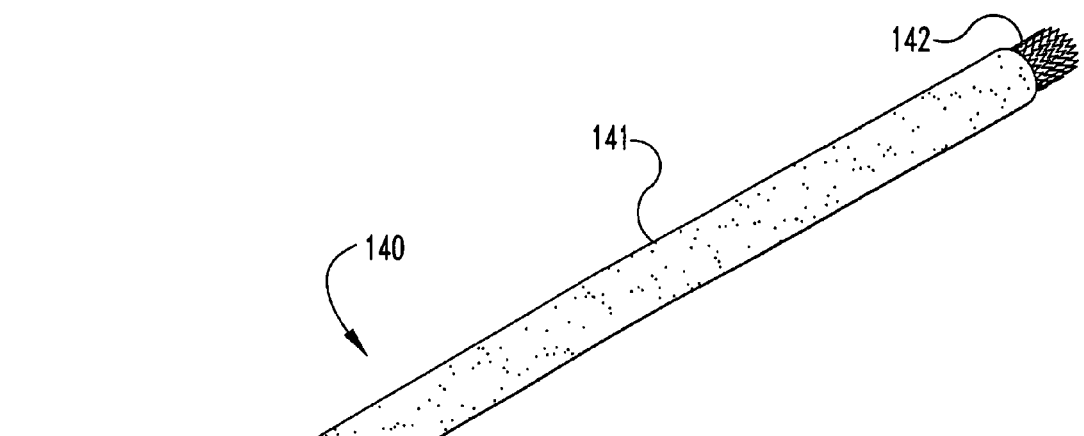
FIG. 34 depicts an illustrative occlusion device of the invention.
Figure 35A:
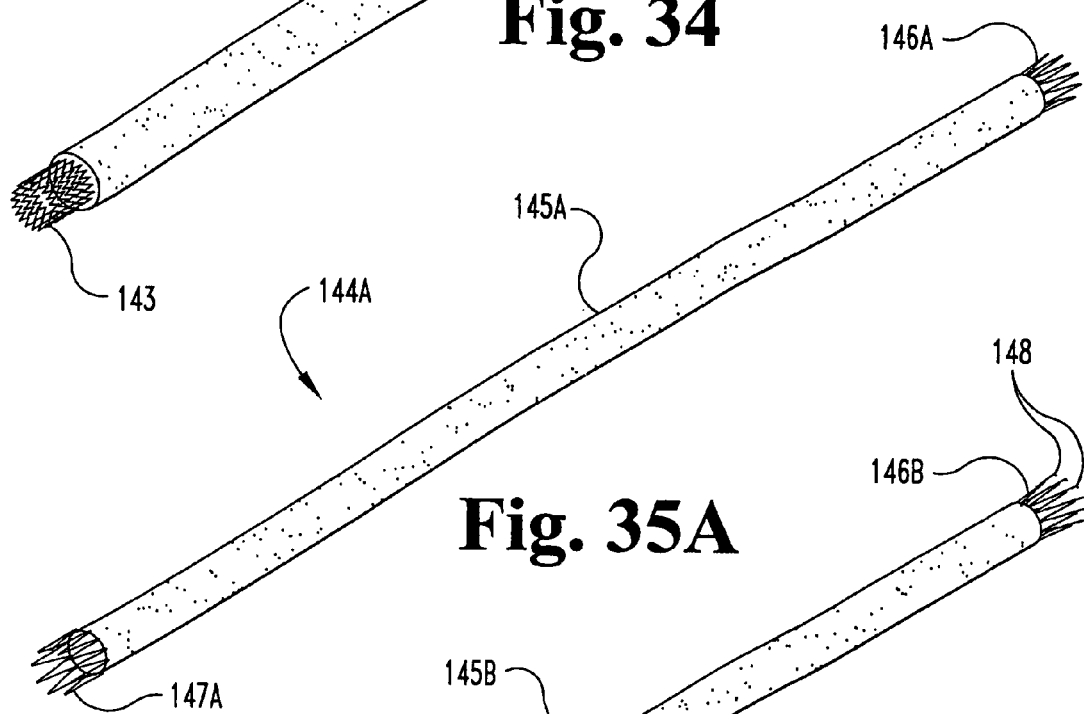
FIG. 35A depicts an illustrative occlusion device of the invention.
Figure 35B:
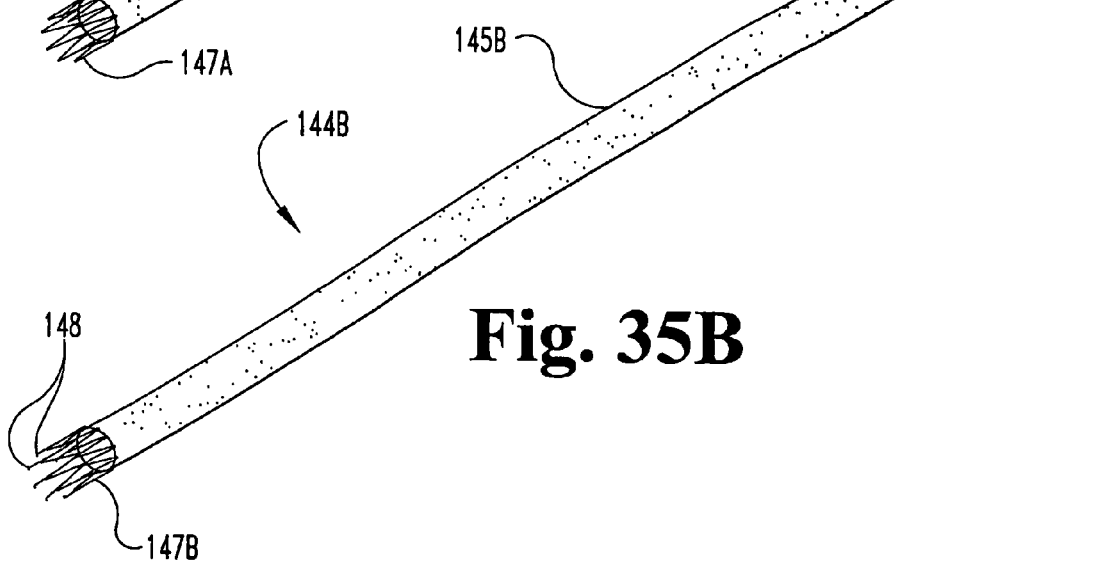
FIG. 35B depicts an illustrative occlusion device of the invention.

With reference to FIG. 33-35B, shown are various occlusion devices of the invention including occlusion bodies and self-expanding or forcibly (e.g. balloon) expandable stents secured to the ends of the occlusion bodies for providing points of securement within a vascular vessel. FIG. 33 shows device 136 having occlusion body 137, such as a strip or tube of occlusion material, having first and second square stents 138 and 139 attached to the ends thereof. Square-shaped stents 138 and 139 can, for example, be constructed as described in U.S. Pat. Nos. 6,200,336 and 6,508,833. FIG. 34 discloses a vascular occlusion device 140 having an occlusion body 141 such as a strip or tube of occlusion material having secured at the ends thereof stents such as those ZILVER® stents sold by Cook, Inc., Bloomington, Ind. (elements 142 and 143). FIG. 35A shows an occlusion device 144A having an occlusion body 145A such as a strip or tube of occlusion material having attached to ends thereof Z-stents 146A and 147A such as those sold by Cook, Inc. FIG. 35B discloses an occlusion device 144B similar to that depicted in FIG. 35A but further comprising barbs 148 attached to the struts of the stents 146B, 147B located at each device end. For more information on suitable barb configurations and methods of placing or mounting barbs on stents, reference can be made to U.S. Pat. No. 5,720,776 and App. 2001/0039450.

In the above-described embodiments incorporating stents, coils, filter-like elements or other anchor devices, attachment of the occluder material to the anchor device may be achieved by suturing, bonding, heat-induced welding (including laser welding), or any other suitable technique. As well, where stents are utilized, any lumen of the stent(s) may be spanned and closed by a biomaterial, including a remodelable biomaterial as described herein, to facilitate the occlusion procedure.

The material used in the formation of vascular occlusion devices of the invention can be any material suitable for occluding a vascular vessel of interest. In this regard, the occlusion material may be a synthetic material such as a polymeric material, a naturally-derived material, or a metallic material such as stainless steel. Illustrative synthetic materials may include biodegradable or non-biodegradable materials. These include, for example, synthetic biocompatible polymers such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, woven DACRON®, polyvinyl alcohol foam, a hydrogel, or mixtures or copolymers thereof; polylactic acid, polyglycolic acid or copolymers thereof, a polyanhydride, polycaprolactone, polyhydroxy-butyrate valerate, polyhydroxyalkanoate, or another biodegradable polymer.

Reconstituted or naturally-derived collagenous materials and/or another source of tissue, such as vascular vessels, can also be used as occlusion materials in the present invention. Such materials that are at least bioresorbable will provide advantage in the present invention, with materials that are bioremodelable and promote cellular invasion and ingrowth providing particular advantage. Bioremodelable materials may be used in this context to promote cellular growth within the lumen of the occluded vessel. This helps to guard against re-establishment of patency of the vessel through biologic processes after the occlusion procedure is completed.

Suitable bioremodelable materials can be provided by collagenous extracellular matrix materials (ECMs) possessing biotropic properties. These can be delivered to the vessel in a lyophilized or otherwise dried, or hydrated state, or additionally or alternatively in a gel or otherwise flowable (and optionally hardenable) state. For example, suitable collagenous materials include ECMs such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa.

As prepared and used, the submucosa material and any other ECM used, may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the submucosa tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the occlusion devices include, for example, antibiotics, thrombus-promoting substances such as blood clotting factors, e.g. thrombin, fibrinogen, and the like. These substances may be applied to the occlusion device as a pre-manufactured step, immediately prior to the procedure (e.g. by soaking the material in a solution containing a suitable antibiotic such as cefazolin), or during or after deployment of the occlusion device in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. The ECM material used in the invention is preferably disinfected with an oxidizing agent, particularly a peracid, such as peracetic acid. These and additional properties of submucosa or other ECM tissue taught in U.S. Pat. No. 6,206,931 may be characteristic of the submucosa tissue used in the present invention.

Figure 36:
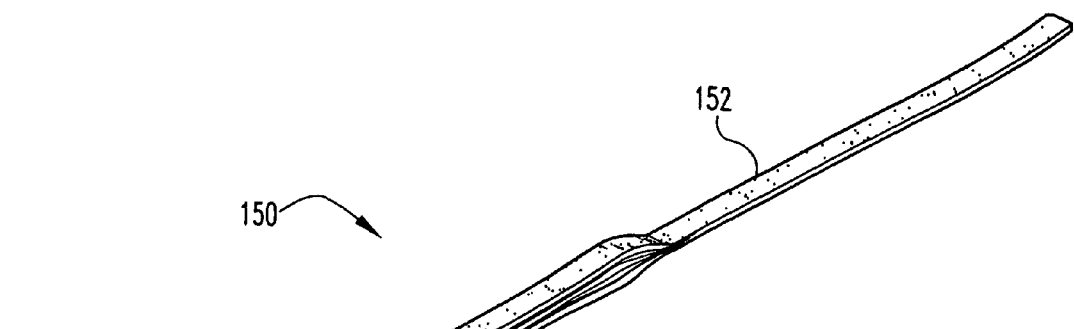
FIG. 36 depicts an illustrative occlusion device of the invention.

When used in the invention, collagenous materials such as ECMs can be in a hydrated or dried state in the product as packaged and/or when delivered. Suitable drying techniques include, for example, air drying, lyophilization techniques including freeze-drying and evaporative cooling, and vacuum-drying e.g. as occurs in vacuum pressing processes. In addition, occluder devices of the invention can include collagenous materials such as ECM materials, a portion of which have been dried by one technique and another portion of which have been dried by another, differing technique. Illustratively, an occluder device may be provided with a more pliant portion that has been dried under lyophilization conditions, and a less pliant portion that has been dried by air-drying or under vacuum pressing conditions. For instance, shown in FIG. 36 is an occluder device 150 that includes a relatively pliant, lyophilized, fan-folded portion 151 attached at one end to a more rigid vacuum-pressed portion 152 which may be formed as a cord or rope. In this manner, the device 150 can be advanced into a vein or other vessel (e.g. from a sheath or other cannulated device) with the fan-folded portion 151 as the leading end, while using the more rigid vacuum-pressed portion 152 to push the fan-folded portion 151. The vacuum-pressed portion 152 can optionally be sufficiently long to extend out of the percutaneous entry site and effectively serve as a pusher rod. After withdrawal of the sheath, the vacuum-pressed portion can be trimmed at the skin and tucked into the percutaneous access site.

Figure 37:
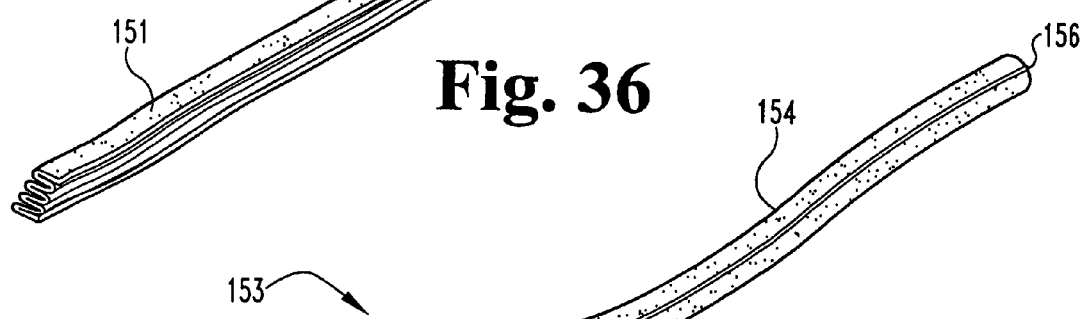
FIG. 37 depicts an illustrative occlusion device of the invention.

FIG. 37 shows another occluder device embodiment including a collagenous material such as an ECM, and a more rigid component. Occluder device 153 includes an elongate body 154 of ECM or other collagenous material, and a more rigid elongate element 155 connected to the body 154. For example, element 155 can be connected to the body 154 at least at or near the distal end 156 of the body 154, which will serve as the leading end of the device 153 during delivery, e.g. from a sheath or other cannulated device. In some embodiments, element 155 will be connected to body 154 at multiple points or continuously along the length of body 154. Element 155 can have a length sufficient to extend from the cannulated device. Thereby, element 155 can be held in place during withdrawal of the cannulated device, to facilitate maintaining the position of the distal end 156 of body 154 in the vein or other vessel during such withdrawal. In this regard, in one convenient embodiment, a splitable sheath or other cannulated device can be employed during delivery, and split around rigid element 155 as the sheath is withdrawn from the patient.

If element 155 is made from a permanently implantable material, element 155 can be trimmed and left implanted in the patient along with body 154. For example, element 155 may be comprised of a bioresorbable and/or bioremodelable material such as a synthetic polymer or collagen, including an ECM material. When element 155 and body 154 each comprise an ECM such as submucosa or another collagenous material, element 155 may for example be air-dried or vacuum pressed to be more rigid than body 154, which may be lyophilized. In these embodiments, element 155 and body 154 may be formed of a single piece of material, or multiple pieces of material attached together, e.g. by bonding or suturing with a bioresorbable or other material.

Figure 38:
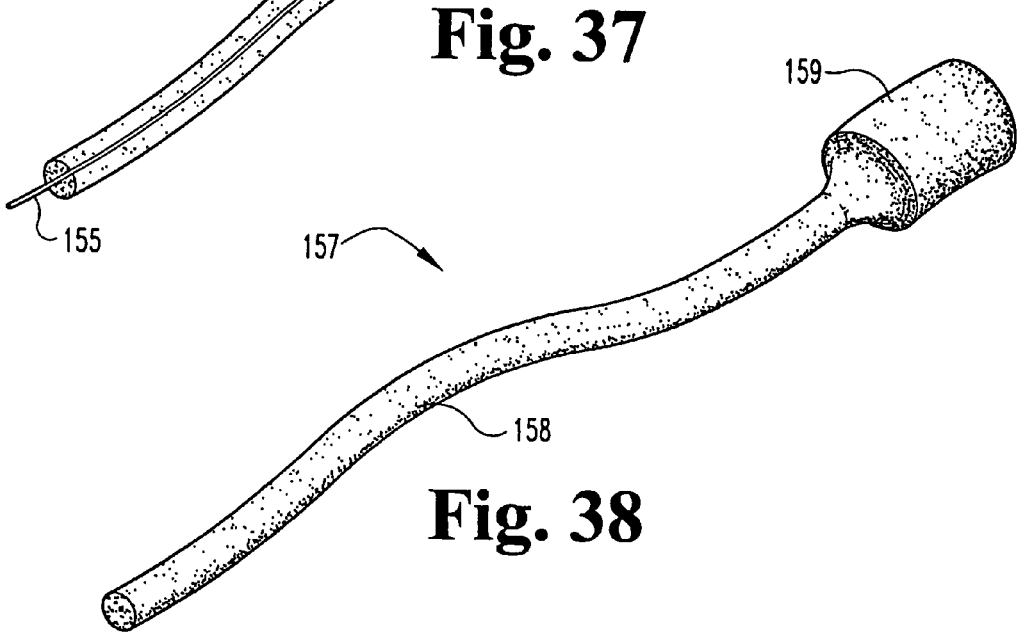
FIG. 38 depicts an illustrative occlusion device of the invention.

Shown in FIG. 38 is another occluder device embodiment 157 having an elongate body 158 and a distal anchoring end 159. Distal anchoring end 159 is configured to expand and contact the walls of the vein or other vessel after delivery from the end of a cannulated device, sufficiently to facilitate maintaining the end 159 and connected body 158 in place during withdrawal of the cannulated device. Distal anchoring end 159 may be made from the same material or a different material as elongate body 158. For example, body 158 and distal anchoring end 159 may both be made of a resorbable substance such as a collagenous material (e.g. containing an ECM such as submucosa), with anchoring end 159 being comprised of a relatively highly expandable porous material such as sponge or foam, and body 158 being comprised of a less expandable ribbon. The anchoring end 159 and body 158 may for example be integrally formed, or may be separate pieces attached to one another by bonding, sutures or other means. As in certain other embodiments described herein, the ribbon or other body 158 may be sufficiently long to extend to the percutaneous exit site, where it can be trimmed after delivery.

Figure 39:
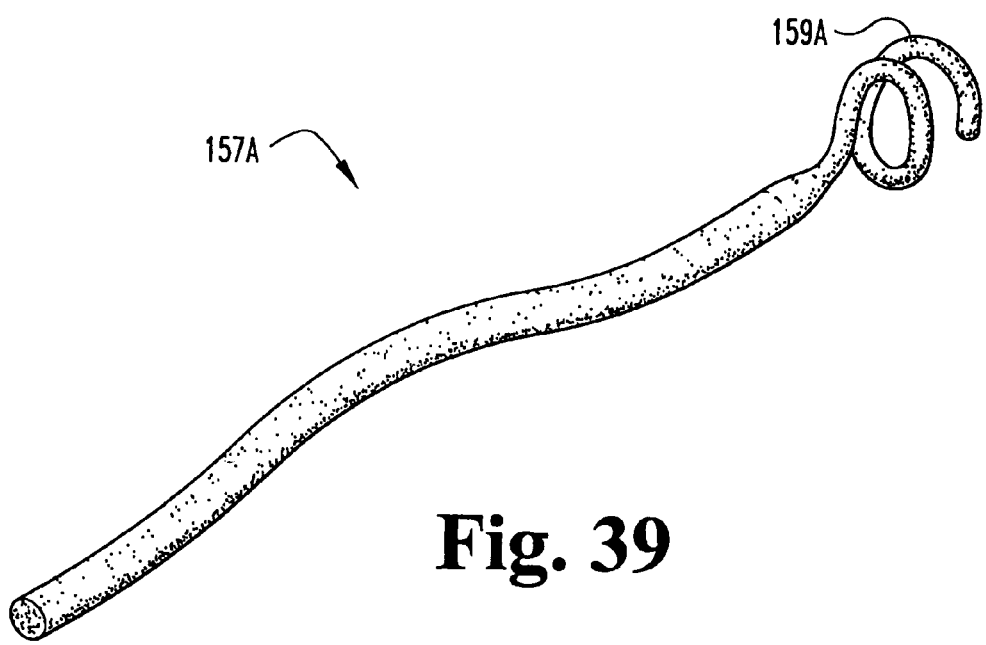
FIG. 39 depicts an illustrative occlusion device of the invention.

As illustrated in FIG. 39, in another embodiment 157A similar to that described in conjunction with FIG. 38, an anchoring end 159A is provided by a coiled portion that is collapsed during receipt within the cannulated delivery device, and which radially expands upon exiting the device. When an ECM-containing or other collagenous material is used for anchoring end 159A, the material can be lyophilized, vacuum-pressed or otherwise dried in the coiled or other radially-expanding configuration, to set a shape memory to the material.

Figure 40:
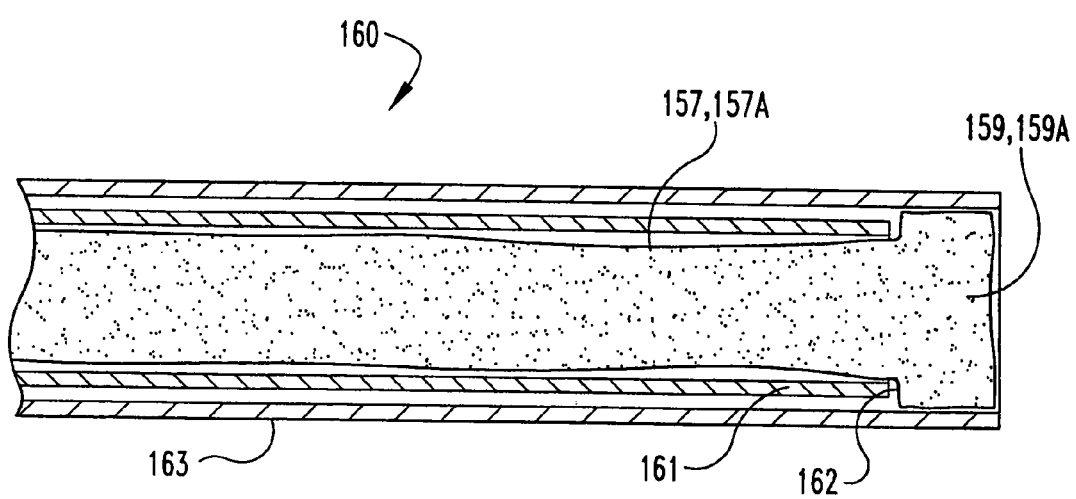
FIG. 40 depicts an illustrative deployment embodiment of the invention.

As shown in FIG. 40, devices 157 and 157A may be delivered in a dual-sheath system 160, in which an inner sheath 161 extends to the trailing edge 162 of the anchoring end 159,159A, and an outer sheath 163 extends over the anchoring end 159,159A. In this manner, after advancement into the vessel to be occluded, outer sheath 163 can be withdrawn to release anchoring end 159,159A to expand and contact the vessel walls, whereafter inner sheath 161 can be withdrawn while anchoring end 159,159A resists withdrawal of the device 157,157A from the vessel. It will be understood that such a dual-sheath system may be used in conjunction with any similar occluder device having an expandable anchoring feature and an elongate portion, including expandable features such as stents, filter-type baskets, coils, and the like.

It will be also understood that devices similar to those shown in FIGS. 38 and 39, except having more than one anchoring portion, e.g. having anchoring ends at both ends, are also contemplated as being within the invention. Such devices having an anchoring portion at each end may be deployed fully into the lumen of the vein or other vessel to be occluded, with the anchoring ends contacting the vessel walls and stabilizing the position of the devices in the vessel.

Occlusion devices of the invention will generally be of sufficient dimension to achieve occlusion of the desired stretch of vascular vessel, either alone or in combination with other similar or differing devices. In certain embodiments, the occlusion device will have a length of at least about 10 cm, and in many situations at least about 20 cm. Indeed, for preferred occlusion procedures involving a significant stretch of an artery or vein, occlusion devices having lengths greater than 30 cm will be used. Illustratively, in the occlusion of the greater saphenous vein in human adolescents or adults, occlusion devices having lengths of at least about 40 cm or 50 cm can be used.

While discussions above focus upon occluding the greater saphenous vein via access at the knee level, the greater saphenous vein may also be accessed at a lower level, e.g. near the ankle. During such access, any or all of the greater saphenous vein occurring between the ankle and the sapheno-femoral junction may be subjected to occlusion. Other veins in the leg(s) that may be involved in the varicose vein condition may also be occluded, alternatively or in addition to the greater saphenous vein. For example, the lesser saphenous vein, or varicose veins themselves, may be occluded and obliterated in accordance with the invention. Further, other veins or arteries in the leg(s) or elsewhere in the body may be occluded within the scope of the present invention.

Percutaneously-conducted occlusion procedures of the invention will typically be performed under local anesthesia. In addition, after completion of the procedure, it may be beneficial to use graduated compression stockings in the occluded area, for example for a week or more. Compression of the occluded area may serve to facilitate permanent closure of the occluded vessel, for example when applied during a remodeling period during which tissue ingrowth into the occluded lumen occurs.

Sheaths, dilators, wire guides and needles used in the present invention can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators can be made from conventional dilator/catheter type materials such as polyethylene, polyamide, polyurethane or vinyl, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

Delivery sheaths used in the invention will have a lumen diameter sized to allow for the introduction of a sufficient amount of occlusion material to occlude the artery or vein of interest. Illustratively, the inner diameter (I.D.) of the final delivery sheath can range from about 8 French up to about 40 French.

As is conventional, the distal ends of the catheters, sheaths, dilators, wires or other components used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification. As well, distal and/or proximal ends and/or other locations on occluder devices of the invention may include markers for non-invasive imaging, including imageable materials such as those discussed above as well as substances that can be applied to ECMs or other collagenous materials, e.g. substances containing tantalum, barium, iodine, or bismuth, e.g. in powder form.

The invention also encompasses medical kits, such as, for example, an elongate puncture device, a cannulated guiding device, a sheath, a guide wire configured for engagement of an occlusion device, and an inventive occlusion device, sealed within sterile medical packaging. The final, packaged products are provided in a sterile condition. This may be achieved, for example, by gamma, e-beam or other irradiation techniques, ethylene oxide gas, or any other suitable sterilization technique, and the materials and other properties of the medical packaging will be selected accordingly. The occlusion device may be packaged wet or after it is dried.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected. All publications cited herein are hereby incorporated by reference in their entirety as if each had been individually incorporated by reference and fully set forth. In addition, U.S. Provisional Patent Application Ser. No. 60/470,611, filed May 14, 2003 and entitled, "Vessel Closure Device, Delivery Apparatus and Method of Delivering the Closure Device," is hereby incorporated herein by reference in its entirety.

What is claimed is:

1. A method for occluding a venous vessel having an inside wall, comprising:
    providing a delivery device including a first sheath having a lumen and a second sheath having a lumen, with the second sheath received in the lumen of the first sheath;
    providing an occlusion device positioned in the delivery device, the occlusion device including only a single anchoring member configured to expand to forcibly contact the inside wall of the venous vessel and an elongate occluding body extending away from the anchoring member, wherein the anchoring member comprises an expandable sponge body anchoring member, wherein the expandable sponge body anchoring member resides outside of the second sheath and within the lumen of the first sheath, and wherein the elongate occluding body resides within the lumen of the second sheath;
    accessing the venous vessel through an access point;
    inserting the delivery device into the venous vessel through said access point;
    advancing the delivery device through the venous vessel away from the access point;
    deploying the sponge body anchoring member out of the lumen of the first sheath and into the venous vessel, wherein the sponge body anchoring member expands to forcibly contact the inside wall of the venous vessel so as to become anchored in the venous vessel and to fill the lumen of the venous vessel with the sponge body anchoring member at a location spaced from said access point; and
    removing the delivery device from the venous vessel through said access point, wherein the anchoring member inhibits migration of the elongate occluding body in the venous vessel during said removing such that the elongate occluding body is drawn from the lumen of the second sheath to remain implanted in the venous vessel along an elongate stretch of the venous vessel occurring between said anchoring member and the access point, with the elongate occluding body occluding the flow of blood through said venous vessel along said elongate stretch.

2. The method according to claim 1, wherein the elongate occluding body remains implanted within the venous vessel traversing at least one junction between said venous vessel and a second venous vessel.

3. The method according to claim 2, wherein the second venous vessel is a perforator or communicator vessel.

4. The method according to claim 3, wherein said venous vessel is a superficial venous vessel.

5. The method according to claim 4, wherein said venous vessel is a saphenous vein.

6. The method according to claim 1, wherein said elongate occluding body comprises a remodelable material derived from a collagenous tissue source.

7. The method according to claim 1, wherein said elongate occluding body comprises an expandable porous material.

8. The method according to claim 7, wherein said expandable porous material comprises an extracellular matrix material.

9. The method according to claim 1, wherein said elongate occluding body has a length of at least about 10 cm.

10. The method according to claim 1, wherein said elongate occluding body has a length of at least about 20 cm.

11. The method according to claim 1, wherein said expandable sponge body anchoring member comprises a collagenous material.

12. The method according to claim 11, wherein said collagenous material comprises an extracellular matrix material.

13. The method according to claim 1, wherein said expandable sponge body anchoring member and said elongate occluding body are integrally formed with one another.

14. The method according to claim 1, wherein said expandable sponge body anchoring member comprises a resorbable material.

15. The method according to claim 1, wherein said expandable sponge body anchoring member and said elongate occluding body are separate pieces attached to one another.

16. The method according to claim 1, wherein while said occlusion device is positioned in said delivery device, the expandable sponge body anchoring member has an outer diameter greater than the diameter of the lumen of the second sheath.

17. The method according to claim 1, wherein said elongate occluding body is of sufficient length to extend from said anchoring member to said access point, and wherein the method also includes trimming said elongate occluding body from said access point.

18. A method for occluding a venous vessel having an inside wall, comprising:
    providing a delivery device having a lumen;
    providing an occlusion device positioned in the delivery device lumen, the occlusion device having a length of at least about 10 cm and including only a single anchoring member configured to expand to forcibly contact the inside wall of the venous vessel and an elongate occluding body extending away from the anchoring member, the anchoring member and the elongate occluding body comprising the same material, and the anchoring member and the elongate occluding body both being fully received within the delivery device lumen;
    accessing the venous vessel through an access point;
    inserting the delivery device into the venous vessel through said access point;
    advancing the delivery device through the venous vessel away from the access point with the anchoring member and the elongate occluding body both being fully received within the delivery device lumen;
    deploying the anchoring member out of the lumen of the delivery device and into the venous vessel, wherein the anchoring member expands to forcibly contact the inside wall of the venous vessel so as to become anchored in the venous vessel at a location spaced from said access point; and removing the delivery device from the venous vessel through said access point, wherein the anchoring member inhibits migration of the elongate occluding body in the venous vessel during said removing such that the elongate occluding body is drawn from the lumen of the delivery device to remain implanted in the venous vessel along an elongate stretch of the venous vessel occurring between said anchoring member and the access point, with the elongate occluding body occluding the flow of blood through said venous vessel along said elongate stretch.

19. The method of 18, wherein the anchoring member and the elongate occluding body each comprise an extracellular matrix material.

20. The method of 19, wherein the anchoring member comprises an extracellular matrix sponge or foam material.

21. The method of 18, wherein the elongate occluding body and the anchoring member are integrally formed.

22. The method of 18, wherein the elongate occluding body and the anchoring member are formed as separate pieces and attached to one another.

23. The method of 18, wherein the anchoring member comprises an expandable porous material.

24. The method of claim 15, wherein:
said delivery device includes a first sheath providing said lumen as a first lumen and a second sheath providing a second lumen, with the second sheath received in the first sheath; and
while said occlusion device is positioned in said delivery device, the anchoring member resides outside of the second sheath and within the first lumen, and the elongate occluding body resides within the second lumen.

25. A method for occluding a venous vessel having an inside wall, comprising:
providing a delivery device having a lumen;
providing an occlusion device positioned in the delivery device lumen, the occlusion device including only a single anchoring member configured to expand to forcibly contact the inside wall of the venous vessel and an elongate occluding body extending away from the anchoring member, the anchoring member comprising an extracellular matrix sponge material, and the anchoring member and elongate occluding body both being fully received within the lumen of the delivery device;
accessing the venous vessel through an access point;
inserting the delivery device into the venous vessel through said access point;
advancing the delivery device through the venous vessel away from the access point with the anchoring member and elongate occluding body both fully received within the lumen of the delivery device;
deploying the anchoring member out of the lumen of the delivery device and into the venous vessel, wherein the anchoring member expands to forcibly contact the inside wall of the venous vessel so as to become anchored in the venous vessel and fill the venous vessel with the sponge material at a location spaced from said access point; and
removing the delivery device from the venous vessel through said access point, wherein the anchoring member inhibits migration of the elongate occluding body in the venous vessel during said removing such that the elongate occluding body is drawn from the lumen of the delivery device to remain implanted in the venous vessel along an elongate stretch of the venous vessel occurring between said anchoring member and the access point, with the elongate occluding body occluding the flow of blood through said venous vessel along said elongate stretch.

26. The method of 25, wherein the occlusion device has a length of at least about 10 cm.

27. The method of 25, wherein the elongate occluding body comprises an extracellular matrix material.

28. The method of 27, wherein the elongate occluding body and the anchoring member are integrally formed.

29. The method of 27, wherein the elongate occluding body and the anchoring member are formed as separate pieces and attached to one another.

30. The method of 25, wherein the extracellular matrix sponge material is dried in a radially-expandable configuration.

31. The method of claim 25, wherein:
said delivery device includes a first sheath providing said lumen as a first lumen and a second sheath providing a second lumen, with the second sheath received in the first sheath; and
while said occlusion device is positioned in said delivery device, the anchoring member resides outside of the second sheath and within the first lumen, and the elongate occluding body resides within the second lumen.

* * * * *